US007252753B2

(12) United States Patent

Rosenbaum et al.

(10) Patent No.: US 7,252,753 B2

(45) Date of Patent: Aug. 7, 2007

(54) DIELECTRIC FLUIDS AND PROCESSES FOR MAKING SAME

(75) Inventors: John M. Rosenbaum, Richmond, CA (US); Nadine L. Yenni, Sonoma, CA (US); Joseph M. Pudlak, Vallejo, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 429 days.

(21) Appl. No.: 11/000,382

(22) Filed: Dec. 1, 2004

(65) Prior Publication Data

US 2006/0113216 A1 Jun. 1, 2006

(51) Int. Cl.
*C07C 5/22* (2006.01)

(52) U.S. Cl. ........................... 208/14; 208/17; 208/18; 252/570; 585/734; 585/738; 585/739

(58) Field of Classification Search .................... None
See application file for complete search history.

(56) References Cited

U.S. PATENT DOCUMENTS

| | | | |
|---|---|---|---|
| 3,773,650 | A | 11/1973 | Hislop et al. |
| 3,775,288 | A | 11/1973 | Eagen et al. |
| 3,852,207 | A | 12/1974 | Stangeland et al. |
| 3,904,513 | A | 9/1975 | Fischer et al. |
| 3,948,789 | A | 4/1976 | Brooks |
| 4,082,866 | A | 4/1978 | Link |
| 4,121,275 | A | 10/1978 | Ross et al. |
| 4,147,646 | A | 4/1979 | Cappo |
| 4,157,294 | A | 6/1979 | Iwao et al. |
| 4,347,121 | A | 8/1982 | Mayer et al. |
| 4,440,871 | A | 4/1984 | Lok et al. |
| 4,477,333 | A | 10/1984 | Hafez |
| 4,568,663 | A | 2/1986 | Mauldin |
| 4,673,487 | A | 6/1987 | Miller |
| 4,753,745 | A | 6/1988 | Kostuyk et al. |
| 4,810,357 | A | 3/1989 | Chester et al. |
| 4,880,553 | A | 11/1989 | Kostuyk et al. |
| 4,943,424 | A | 7/1990 | Miller |
| 5,135,638 | A | 8/1992 | Miller |
| 5,158,665 | A | 10/1992 | Miller |
| 5,282,958 | A | 2/1994 | Santilli et al. |
| 6,083,889 | A | 7/2000 | Angelo et al. |
| 6,090,989 | A | 7/2000 | Trewella et al. |
| 6,468,417 | B1 | 10/2002 | Biscardi et al. |
| 6,485,659 | B1 | 11/2002 | Goedde et al. |
| 6,573,223 | B1 | 6/2003 | Vinci |
| 6,579,441 | B1 | 6/2003 | Biscardi et al. |
| 6,585,917 | B2 | 7/2003 | Sletson et al. |
| 6,599,864 | B1 | 7/2003 | Bertomeu |
| 6,613,250 | B2 | 9/2003 | McShane et al. |
| 6,680,157 | B1 | 1/2004 | Fedynyshyn |
| 2002/0139962 | A1 | 10/2002 | Fefer et al. |

FOREIGN PATENT DOCUMENTS

| | | | |
|---|---|---|---|
| EP | 105 631 | | 3/1988 |
| EP | 278 693 | | 6/1992 |
| EP | 0 458 574 | B1 | 10/1993 |
| EP | 0 609 079 | | 1/1994 |
| EP | 0 776 959 | A2 | 6/1997 |
| EP | 0 668 342 | B1 | 8/1999 |
| JP | 09279160 | A | 10/1997 |
| JP | 2001-195920 | | 7/2001 |
| JP | 2004-163858 | | 6/2004 |
| WO | 00/014179 | | 3/2000 |
| WO | 00/014183 | | 3/2000 |
| WO | 00/014187 | | 3/2000 |
| WO | 00/014188 | | 3/2000 |
| WO | 01/018156 | A1 | 3/2001 |
| WO | 02/064710 | A2 | 8/2002 |
| WO | 02/070629 | A1 | 9/2002 |
| WO | 02/070630 | A1 | 9/2002 |
| WO | 02/070631 | A2 | 9/2002 |
| WO | WO 02/070636 | A | 9/2002 |
| WO | WO 05/066314 | A1 | 7/2005 |
| WO | WO 05/066319 | A1 | 7/2005 |
| WO | WO 05/113734 | A2 | 12/2005 |

OTHER PUBLICATIONS

Netherlands Search Report from NL 1030559 mailed Aug. 24, 2006.

U.S. Appl. No. 11/000,374 "Dielectric Fluids and Processes for Making Same", inventor Rosenbaum, et al., filed Dec. 1, 2004.

U.S. Appl. No. 10/744,389, "Composition of Lubricating Base Oil with High Monocycloparaffins and Low Multicycloparaffins", Inventors Abernathy, Kramer, Rosenbaum, Miller and Krug, filed Dec. 23, 2004.

U.S. Appl. No. 10/744,870, "Process for Manufacturing Lubricating Base Oil with High Monocycloparaffins and Low Multicycloparaffins", Inventors Abernathy, Kramer, Rosenbaum, Miller and Krug, filed Dec. 23, 2003.

McShane, C. Patrick, "New Safety Dielectric Coolants for Distribution and Power Transformer", *IEEE Industry Applications Magazine*, May-Jun. 2000, pp. 24-32.

Gatto, V.J., et al., "The Influence of Chemical Structure on the Physical Properties and Antioxidant Response of Hydrocracked Base Stocks and Polyalphaolefins", *J. Synthetic Lubrication* vol. 19, No. 1 (Apr. 2002), pp. 3-18.

(Continued)

*Primary Examiner*—Tam M. Nguyen

(74) *Attorney, Agent, or Firm*—Buchanan Ingersoll & Rooney PC

(57) ABSTRACT

Dielectric fluids comprising oil fractions derived from highly paraffinic wax are provided. Further provided are processes for making these dielectric fluids comprising oil fractions derived from highly paraffinic wax. The dielectric fluids are useful as insulating and cooling mediums in new and existing power and distribution electrical apparatus, such as transformers, regulators, circuit breakers, switchgear, underground electrical cables, and attendant equipment.

35 Claims, No Drawings

OTHER PUBLICATIONS

Barrer, R.M., "Zeolites, Science and Technology" edited by F.R. Rodriques, et al, NATO ASI Series, (1984), pp. 74-76.

Baerlocher, Ch., et al., "Atlas of Zeolite Framework Types", Fifth Revised Edition, Elsevier, New York, (2001), pp. 10-15.

Anderson, et al., "Reactions on ZSM-5-Type Zeolite Catalysts", *J. Catalysis* vol. 58, (1979), pp. 114-130.

Gruse, William A. and Donald R. Stevens, Chemical Technology of Petroleum, 3rd Edition, McGraw-Hill Book Company, Inc., New York, (1960), pp. 566-570.

Kramer, D.C., et al., "Influence of Group II & III Base Oil Composition on VI and Oxidation Stability", NLGI Spokesman, vol. 63, No. 10, (Jan. 2000), pp. 20-39.

He Xiu-Yun et al., "Commercial Application of Isodewaxing Technology", *Petroleum Processing and Petrochemicals* 32(4), (2001), pp. 14-16, English translation.

DIELECTRIC FLUIDS AND PROCESSES FOR MAKING SAME

FIELD OF THE INVENTION

The present invention relates to insulating dielectric fluids comprising oil fractions derived from highly paraffinic wax. The present invention further relates to processes for making these dielectric fluids comprising oil fractions derived from highly paraffinic wax.

BACKGROUND OF THE INVENTION

Dielectric fluids are fluids that can sustain a steady electric field and act as an electrical insulator. Accordingly, dielectric fluids serve to dissipate heat generated by energizing components and to insulate those components from the equipment enclosure and from other internal parts and devices. Among the properties of a dielectric fluid which affect its ability to function effectively and reliably include flash and fire point, heat capacity, viscosity over a range of temperatures, impulse breakdown strength, gassing tendency, and pour point. Due the varying properties of dielectric fluids, they are often defined by these properties rather than by a specific composition.

Dielectric fluids have traditionally been manufactured from cycloparaffinic base oils, silicone oils, or synthetic organic esters. Mineral oil based dielectric fluids have been extensively used because of their wide availability, low cost, and physical properties; however, mineral oils have relatively low flash and fire points. Polychlorinated bi-phenyls (PCBs) were developed as alternative dielectric fluids. PCBs have excellent dielectric properties and they are far less flammable than mineral oils. Government agencies, at one time, mandated the use of PCBs whenever there was a safety concern related to fluid flammability. Unfortunately PCBs have turned out to be an environmentally hazardous material. Silicone oils and high-molecular weight hydrocarbons currently rank as the most popular choices in applications requiring less flammable fluid. To a much lesser extent, synthetic and natural ester-based fluids and synthetic hydrocarbons are also used.

As the supply of oils traditionally used in dielectric fluids is limited, dielectric fluids are becoming increasingly expensive. Further, commercial demand for such oils may soon exceed their supply.

There has been research into developing processes for making oil compositions useful as an electrical or transformer oil and into oil compositions useful an electrical or transformer oil.

By way of example, EP 0 458 574 B1, U.S. Pat. No. 6,083,889, and JP2001195920 disclose processes for producing formulated transformer oil and oil compositions useful as an electrical or transformer oil.

It is well known in the art to produce synthetic oils and there have been many developmental attempts at producing synthetic oils with high performance characteristics. By way of example, EP 0 776 959 A2, EP 0 668 342 B1, WO 00/014179, WO 00/14183, WO 00/14187, WO 00/14188, WO 01/018156 A1, WO 02/064710 A2, WO 02/070629 A1, WO 02/070630 A1, and WO 02/070631 A2 are directed to synthetic lubricant oil compositions and methods for producing the synthetic lubricant oil compositions.

There remains a need for dielectric fluids having desirable properties, including, high fire point, high flash point, excellent dielectric breakdown, good heat capacity, and excellent impulse breakdown strength. There also remains a need for an abundant and economical source for or an efficient and economical process for producing these dielectric fluids.

SUMMARY OF THE INVENTION

The present invention relates to processes for producing dielectic fluids comprising one or more oil fractions derived from highly paraffinic wax, wherein the dielectric fluids exhibit high dielectric breakdown, high flash point, and high fire point.

In one embodiment, the present invention relates to a process for producing a dielectric fluid. The process comprises providing a highly paraffinic wax, and hydroisomerizing the highly paraffinic wax using a shape selective intermediate pore size molecular sieve comprising a noble metal hydrogenation component under conditions of about 600° F. to about 750° F. to provide an isomerized oil. The isomerized oil is fractionated to provide at least one oil fraction having a $T_{90}$ boiling point $\geqq$950° F., a kinematic viscosity between about 6 cSt and about 20 cSt at 100° C., and a pour point of $\geqq$−14° C., wherein the oil comprises $\geqq$10 weight % molecules with monocycloparaffinic functionality, $\leqq$3 weight % molecules with multicycloparaffinic functionality, and less than 0.30 weight % aromatics. The oil fraction is optionally blended with an effective amount of one or more additives, and a dielectric fluid is isolated having a dielectric breakdown of $\geqq$25 kV as measured by ASTM D877.

In another embodiment the present invention relates to a process for producing a dielectric fluid. The process comprises performing a Fischer-Tropsch synthesis to provide a product stream, and isolating from the product stream a substantially paraffinic wax feed. The substantially paraffinic waxy feed is hydroisomerized using a shape selective intermediate pore size molecular sieve comprising a noble metal hydrogenation component under conditions of about 600° F. to about 750° F., and isomerized oil is isolated. The isomerized oil is fractionated to provide one or more oil fractions having a $T_{90}$ boiling point $\geqq$950° F., a kinematic viscosity between about 6 cSt and about 16 cSt at 100° C., and a pour point of $\geqq$−14° C.; wherein the lubricant base oil comprises $\geqq$10 weight % molecules with monocycloparaffinic functionality, $\leqq$3 weight % molecules with multicycloparaffinic functionality, and less than 0.30 weight % aromatics. The one or more oil fractions are optionally blended with an effective amount of one or more additives, and a dielectric fluid having a dielectric breakdown of $\geqq$25 kV as measured by ASTM D877 is isolated.

DETAILED DESCRIPTION OF THE INVENTION

It has been surprisingly discovered that dielectric fluids comprising certain oil fractions derived from highly paraffinic wax exhibit exceptional properties. Accordingly, the present invention relates to dielectric fluids comprising these oil fractions and processes for their manufacture. Examples of suitable highly paraffinic waxes include Fischer-Tropsch derived wax, slack wax, deoiled slack wax, refined foots oils, waxy lubricant raffinates, n-paraffin waxes, normal alpha olefin (NAO) waxes, waxes produced in chemical plant processes, deoiled petroleum derived waxes, microcrystalline waxes, and mixtures thereof. These highly paraffinic waxes are processed to provide oil fractions having desired properties including a $T_{90}\geqq$950° F., and these oil fractions are used to provide a dielectric fluid having high flash and fire points and having a high dielectric breakdown.

In one preferred embodiment, the highly paraffinic wax is a Fischer-Tropsch derived wax and provides a Fischer-Tropsch derived oil fraction.

It has been surprisingly discovered that dielectric fluids comprising oil fractions derived from highly paraffinic wax, comprising ≧10 weight % molecules with monocycloparaffinic functionality, ≦3 weight % molecules with multicycloparaffinic functionality, and less than 0.30 weight % aromatics and having a $T_{90}$ boiling point ≧950° F.; a kinematic viscosity between about 6 cSt and about 20 cSt at 100° C.; and a pour point of ≧−14° C. exhibit excellent dielectric breakdown of ≧25 kV as measured by ASTM D877 and high flash and fire points. Thus, these oil fractions can advantageously be used as dielectric fluids.

The dielectric fluids according to the present invention comprise one or more oil fractions derived from highly paraffinic wax having a $T_{90}$ boiling point ≧950° F., preferably ≧1000° F., and a kinematic viscosity between about 6 cSt and about 20 cSt at 100° C. The high boiling points of these oil fractions relative to their viscosities provide them with high flash points and high fire points compared to other paraffinic oils of similar viscosities. Even though the oil fractions of the present invention have high boiling points, they still flow well enough to provide effective cooling. The dielectric fluids according to the present invention comprise one or more oil fractions derived from highly paraffinic wax. The dielectric fluids according to the present invention have a dielectric breakdown of ≧25 kV as measured by ASTM D877, preferably ≧30 kV and more preferably ≧40 kV. Preferably, the dielectric fluids according to the present invention have a fire point of ≧310° C., more preferably a fire point of ≧325° C. Preferably, the dielectric fluids according to the present invention have a flash point of ≧280° C.

The dielectric fluids according to the present invention comprise one or more oil fractions comprising ≧10 weight % molecules with monocycloparaffinic functionality, ≦3 weight % molecules with multicycloparaffinic functionality, and less than 0.30 weight % aromatics. The high amounts of monocycloparaffinic functionality provide the oil fractions of the present invention with good solvency, good seal compatibility, and good miscibility with other oils. The very low amounts of multicycloparaffinic functionality provide the oil fractions of the present invention with excellent oxidation stability. The very low amounts of aromatics provide the oil fractions with excellent oxidation stability and UV stability.

The dielectric fluids of the present invention are useful as insulating and cooling mediums in new and existing power and distribution electrical apparatus, such as transformers, regulators, circuit breakers, switchgear, underground electric cables, and attendant equipment.

They are functionally miscible with existing mineral oil based dielectric fluids and are compatible with existing apparatus. These dielectric fluids of the present invention comprising oil fractions derived from highly paraffinic wax can be used in applications requiring high flash point, high fire point, excellent dielectric breakdown, and good additive solubility. In particular, the dielectric fluids of the present invention comprising oil fractions derived from highly paraffinic wax can be used in applications in which a high fire point insulating oil is required. In addition, these oil fractions derived from highly paraffinic wax exhibit excellent oxidation resistance and good elastomer compatibility.

The oil fractions derived from highly paraffinic wax of the present invention are prepared from the highly paraffinic wax by a process including hydroisomerization. Preferably, the highly paraffinic wax is hydroisomerized using a shape selective intermediate pore size molecular sieve comprising a noble metal hydrogenation component under conditions of about 600° F. to 750° F.

In one preferred embodiment, the highly paraffinic wax is a Fischer-Tropsch derived wax and provides a Fischer-Tropsch derived oil fraction. The oil fractions are prepared from the waxy fractions of Fischer-Tropsch syncrude. As such, the Fischer-Tropsch derived oil fractions used as dielectric fluids are made by a process comprising performing a Fischer-Tropsch synthesis to provide a product stream; isolating from the product stream a substantially paraffinic wax feed; hydroisomerizing the substantially paraffinic wax feed; isolating an isomerized oil;

and optionally hydrofinishing the isomerized oil. From the process, a Fischer-Tropsch derived oil fraction, comprising ≧10 weight % molecules with monocycloparaffinic functionality, ≦3 weight % molecules with multicycloparaffinic functionality, and less than 0.30 weight % aromatics and having a $T_{90}$ boiling point ≧950° F.; a kinematic viscosity between about 6 cSt and about 20 cSt at 100° C.; and a pour point of ≧−14° C. is isolated. The herein-recited preferred embodiments of the Fischer-Tropsch oil fraction also may be isolated from the process. Preferably, the paraffinic wax feed is hydroisomerized using a shape selective intermediate pore size molecular sieve comprising a noble metal hydrogenation component under conditions of about 600° F. to 750° F. Examples of processes for making the Fischer-Tropsch derived oil fractions are described in U.S. Ser. No. 10/744,870, filed Dec. 23, 2003, herein incorporated by reference in its entirety. Examples of embodiments of Fischer-Tropsch oil fractions with high monocycloparaffins and low multicycloparaffins are described in U.S. Ser. No. 10/744,389, filed Dec. 23, 2003, herein incorporated by reference in its entirety.

According to the present invention, the dielectric fluids comprise one or more oil fractions derived from highly paraffinic wax containing a relatively high weight percent of molecules with monocycloparaffinic functionality and a relatively low weight percent of molecules with multicycloparaffinic functionality and aromatics. The oil fractions according to the present invention comprise ≧10 weight % molecules with monocycloparaffinic functionality and ≦3 weight % molecules with multicycloparaffinic functionality. In a preferred embodiment, the oil fraction derived from highly paraffinic wax comprises ≧15 weight % molecules with monocycloparaffinic functionality. In another preferred embodiment, the oil fraction derived from highly paraffinic wax comprises ≦2.5 weight percent molecules with multicycloparaffinic functionality. In another preferred embodiment, the oil fraction derived from highly paraffinic wax comprises ≦1.5 weight percent molecules with multicycloparaffinic functionality. In yet another preferred embodiment, the oil fraction derived from highly paraffinic wax comprises a ratio of weight percent of molecules with monocycloparaffinic functionality to weight percent of molecules with multicycloparaffinic functionality of greater than 5. The oil fraction derived from highly paraffinic wax containing a high ratio of weight percent of molecules with monocycloparaffinic functionality to weight percent of molecules with multicycloparaffinic functionality (or high weight percent of molecules with monocycloparaffinic functionality and low weight percent of molecules with multicycloparaffinic functionality) are exceptional dielectric fluids. Even though these oil fractions derived from highly paraffinic wax contain a high paraffins content, they unexpectedly exhibit good solubility for additives and good miscibility with other oils, because cycloparaffins impart additive solubility. These oil fractions derived from highly paraffinic wax are also desirable because molecules with multicycloparaffinic functionality reduce oxidation stability, lower viscosity index, and increase Noack volatility. Models of the effects of molecules with multicycloparaffinic functionality are given in V. J. Gatto, et al, "The Influence of Chemical Structure on the Physical Properties and Antioxidant Response of Hydrocracked Base Stocks and Polyalphaolefins," J. Synthetic Lubrication 19-1, April 2002, pp 3-18.

Accordingly, in a preferred embodiment, the dielectric fluids according to the present invention comprise one or more oil fractions derived from highly paraffinic wax comprising very low weight percents of molecules with aromatic functionality, a high weight percent of molecules with monocycloparaffinic functionality, and a high ratio of weight percent of molecules with monocycloparaffinic functionality to weight percent of molecules with multicycloparaffinic functionality (or high weight percent of molecules with monocycloparaffinic functionality and very low weight percents of molecules with multicycloparaffinic functionality).

The dielectric fluids comprise oil fractions derived from highly paraffinic wax containing greater than 95 weight % saturates as determined by elution column chromatography, ASTM D 2549-02. Olefins are present in an amount less than detectable by long duration $C^{13}$ Nuclear Magnetic Resonance Spectroscopy (NMR). Preferably, molecules with aromatic functionality are present in amounts less than 0.3 weight percent by HPLC-UV, and confirmed by ASTM D 5292-99 modified to measure low level aromatics. In preferred embodiments molecules with aromatic functionality are present in amounts less than 0.10 weight percent, preferably less than 0.05 weight percent, more preferably less than 0.01 weight percent. Preferably, sulfur is present in amounts less than 10 ppm, more preferably less than 5 ppm, and even more preferably less than 1 ppm, as determined by ultraviolet fluorescence by ASTM D 5453-00.

According to the present invention, a dielectric fluid comprising an oil fraction derived from highly paraffinic wax is provided. The insulating dielectric fluid of the present invention may comprise one or more of these oil fractions derived from highly paraffinic wax and having a $T_{90}$ boiling point of greater than or equal to 950° F. The dielectric fluids according to the present invention also may optionally comprise one or more additives. In addition, the dielectric fluids according to the present invention may optionally comprise other oils typically used as dielectric fluids. These other oils may be Fischer-Tropsch derived oils, mineral oil, other synthetic oils, and mixtures thereof. The use of more than one oil allows for upgrading of a less desirable property of one oil with the addition of a second oil having a more preferred property. Examples of properties that may be upgraded with blending are viscosity, pour point, flash and fire points, interfacial tension, and dielectric breakdown.

Definitions and Terms

The following terms will be used throughout the specification and will have the following meanings unless otherwise indicated.

The term "derived from a Fischer-Tropsch process" or "Fischer-Tropsch derived," means that the product, fraction, or feed originates from or is produced at some stage by a Fischer-Tropsch process.

The term "derived from a petroleum" or "petroleum derived" means that the product, fraction, or feed originates from the vapor overhead streams from distilling petroleum crude and the residual fuels that are the non-vaporizable remaining portion. A source of the petroleum derived can be from a gas field condensate.

Highly paraffinic wax means a wax having a high content of n-paraffins, generally greater than 40 weight %, preferably greater than 50 weight %, and more preferably greater than 75 weight %. Preferably, the highly paraffinic waxes used in the present invention also have very low levels of nitrogen and sulfur, generally less than 25 ppm total combined nitrogen and sulfur and preferably less than 20 ppm. Examples of highly paraffinic waxes that may be used in the present invention include slack waxes, deoiled slack waxes, refined foots oils, waxy lubricant raffinates, n-paraffin waxes, NAO waxes, waxes produced in chemical plant processes, deoiled petroleum derived waxes, microcrystalline waxes, Fischer-Tropsch waxes, and mixtures thereof. The pour points of the highly paraffinic waxes useful in this invention are greater than 50° C. and preferably greater than 60° C.

The term "derived from highly paraffinic wax" means that the product, fraction, or feed originates from or is produced at some stage by from a highly paraffinic wax.

Aromatics means any hydrocarbonaceous compounds that contain at least one group of atoms that share an uninterrupted cloud of delocalized electrons, where the number of delocalized electrons in the group of atoms corresponds to a solution to the Huckel rule of 4n+2 (e.g., n=1 for 6 electrons, etc.). Representative examples include, but are not limited to, benzene, biphenyl, naphthalene, and the like.

Molecules with cycloparaffinic functionality mean any molecule that is, or contains as one or more substituents, a monocyclic or a fused multicyclic saturated hydrocarbon group. The cycloparaffinic group may be optionally substituted with one or more, preferably one to three, substituents. Representative examples include, but are not limited to, cyclopropyl, cyclobutyl, cyclohexyl, cyclopentyl, cycloheptyl, decahydronaphthalene, octahydropentalene, (pentadecan-6-yl)cyclohexane, 3,7,10-tricyclohexylpentadecane, decahydro-1-(pentadecan-6-yl)naphthalene, and the like.

Molecules with monocycloparaffinic functionality mean any molecule that is a monocyclic saturated hydrocarbon group of three to seven ring carbons or any molecule that is substituted with a single monocyclic saturated hydrocarbon group of three to seven ring carbons. The cycloparaffinic group may be optionally substituted with one or more, preferably one to three, substituents. Representative examples include, but are not limited to, cyclopropyl, cyclobutyl, cyclohexyl, cyclopentyl, cycloheptyl, (pentadecan-6-yl)cyclohexane, and the like.

Molecules with multicycloparaffinic functionality mean any molecule that is a fused multicyclic saturated hydrocarbon ring group of two or more fused rings, any molecule that is substituted with one or more fused multicyclic saturated hydrocarbon ring groups of two or more fused rings, or any molecule that is substituted with more than one monocyclic saturated hydrocarbon group of three to seven ring carbons. The fused multicyclic saturated hydrocarbon ring group preferably is of two fused rings. The cycloparaffinic group may be optionally substituted with one or more, preferably one to three, substituents. Representative examples include, but are not limited to, decahydronaphthalene, octahydropentalene, 3,7,10-tricyclohexylpentadecane, decahydro-1-(pentadecan-6-yl)naphthalene, and the like.

Kinematic viscosity is a measurement of the resistance to flow of a fluid under gravity. Many lubricant base oils, finished lubricants made from them, and the correct operation of equipment depends upon the appropriate viscosity of the fluid being used. Kinematic viscosity is determined by ASTM D 445-01. The results are reported in centistokes (cSt). The oil fractions derived from highly paraffinic wax of the present invention have a kinematic viscosity of between about 6.0 cSt and 20 cSt at 100° C. Preferably, the oil fractions derived from highly paraffinic wax have a kinematic viscosity of between about 8 cSt and 16 cSt at 100° C.

Viscosity Index (VI) is an empirical, unitless number indicating the effect of temperature change on the kinematic viscosity of the oil. Liquids change viscosity with temperature, becoming less viscous when heated; the higher the VI of an oil, the lower its tendency to change viscosity with temperature. High VI oils are needed wherever relatively constant viscosity is required at widely varying temperatures. VI may be determined as described in ASTM D 2270-93. Preferably, the oil fractions derived from highly paraffinic wax have a viscosity index of between about 130 and 190 and more preferably between about 140 and 180.

Pour point is a measurement of the temperature at which a sample of oil will begin to flow under carefully controlled conditions. Pour point may be determined as described in ASTM D 5950-02. The results are reported in degrees Celsius. Many commercial lubricant base oils have specifications for pour point. When oils have low pour points, they also are likely to have other good low temperature properties, such as low cloud point, low cold filter plugging point, and low temperature cranking viscosity. Cloud point is a measurement complementary to the pour point, and is expressed as a temperature at which a sample of the oil begins to develop a haze under carefully specified conditions. Cloud point may be determined by, for example, ASTM D 5773-95. Oils having pour-cloud point spreads (i.e., the difference between the pour point temperature and the cloud point temperature) below about 35° C. are desirable. Higher pour-cloud point spreads require processing the oil to very low pour points in order to meet cloud point specifications. The oil fractions derived from highly paraffinic wax of the present invention have pour point of ≧−14° C., preferably ≧−12° C.

Noack volatility is defined as the mass of oil, expressed in weight %, which is lost when the oil is heated at 250° C. and 20 mm Hg (2.67 kPa; 26.7 mbar) below atmospheric in a test crucible through which a constant flow of air is drawn for 60 minutes, according to ASTM D5800. A more convenient method for calculating Noack volatility and one which correlates well with ASTM D5800 is by using a thermo gravimetric analyzer test (TGA) by ASTM D6375. TGA Noack volatility is used throughout this disclosure unless otherwise stated. Preferably, the oil fractions derived from highly paraffinic wax of the present invention have a Noack volatility of less than 10 weight % and more preferably less than 5 weight %.

The aniline point test indicates if an oil is likely to damage elastomers (rubber compounds) that come in contact with the oil. The aniline point is called the "aniline point temperature," which is the lowest temperature (° F. or ° C.) at which equal volumes of aniline ($C_6H_5NH_2$) and the oil form a single phase. The aniline point (AP) correlates roughly with the amount and type of aromatic hydrocarbons in an oil sample. A low AP is indicative of higher aromatics, while a high AP is indicative of lower aromatics content. The aniline point is determined by ASTM D611-04. Preferably, the oil fractions derived from highly paraffinic wax of the present invention have an aniline point of 100 to 170° C. Accordingly, the oil fractions derived from highly paraffinic wax exhibit good elastomer compatibility.

The Oxidator BN with L-4 Catalyst Test is a test measuring resistance to oxidation by means of a Dornte-type oxygen absorption apparatus (R. W. Dornte "Oxidation of White Oils," Industrial and Engineering Chemistry, Vol. 28, page 26, 1936). Normally, the conditions are one atmosphere of pure oxygen at 340° F., reporting the hours to absorption of 1000 ml of $O_2$ by 100 g of oil. In the Oxidator BN with L-4 Catalyst test, 0.8 ml of catalyst is used per 100 grams of oil.

The catalyst is a mixture of soluble metal naphthenates in kerosene simulating the average metal analysis of used crankcase oil. The mixture of soluble metal naphthenates simulates the average metal analysis of used crankcase oil. The level of metals in the catalyst is as follows: Copper=6,927 ppm; Iron=4,083 ppm; Lead=80,208 ppm; Manganese=350 ppm; Tin=3565 ppm. The additive package is 80 millimoles of zinc bispolypropylenephenyldithio-phosphate per 100 grams of oil, or approximately 1.1 grams of OLOA® 260. The Oxidator BN with L-4 Catalyst Test measures the response of a finished lubricant in a simulated application. High values, or long times to adsorb one liter of oxygen, indicate good stability. OLOA® is an acronym for Oronite Lubricating Oil Additive®, which is a registered trademark of ChevronTexaco Oronite Company.

Generally, the Oxidator BN with L-4 Catalyst Test results should be above about 7 hours. Preferably, the Oxidator BN with L-4 value will be greater than about 10 hours. Preferably, the oil fractions derived from highly paraffinic wax of the present invention have results greater than about 10 hours. The Fischer-Tropsch derived oil fractions of the present invention have results much greater than 10 hours.

Flash point is the minimum temperature at which heated oil gives off sufficient vapor to form a flammable mixture with air that will ignite when contacted with an ignition source. It is an indicator of the volatility of the oil. According to the present invention, the flash point is determined by ASTM D92. Preferably, the dielectric fluids of the present invention have a flash point of ≧280° C.

Fire point is the minimum temperature at which heated oil gives off sufficient vapor to form a flammable mixture with air that will ignite and sustain burning for a minimum of 5 seconds when contacted with an ignition source. It is an indicator of the combustibility of the oil. According to the present invention, the fire point is determined by ASTM D92. Preferably, the dielectric fluids of the present invention have a fire point of ≧310° C., more preferably ≧325° C.

Dielectric breakdown is the minimum voltage at which electrical flashover occurs in an oil. It is a measure of the ability of an oil to withstand electrical stress at power frequencies without failure. A low value for the dielectric-breakdown voltage generally serves to indicate the presence of contaminants such as water, dirt, or other conducting particles in the oil. Dielectric breakdown is measured according to ASTM D877. The dielectric fluids of the present invention have a dielectric breakdown of ≧25 kV, preferably ≧30 kV, and more preferably ≧40 kV.

Low water content is necessary to obtain and maintain acceptable electrical strength and low dielectric losses in insulation systems. According to the present invention, the water content is determined by ASTM D1533. Preferably, the dielectric fluids of the present invention have a water content of less than 100 ppm, more preferably less than 35 ppm, and even more preferably less than 25 ppm.

Interfacial tension of an oil is the force in dynes per centimeter required to rupture the oil film existing at an oil-water interface. When certain contaminants such as soaps, paints, varnishes, and oxidation products are present in the oil, the film strength of the oil is weakened, thus requiring less force to rupture. According to the present invention, the interfacial tension is determined by ASTM D971. Preferably, the dielectric fluids of the present invention exhibit an interfacial tension of greater than 30, more preferably greater than 35, and even more preferably greater than 40 dyne/cm.

Neutralization number of an oil is a measure of the amount of acidic or alkaline materials present. As oils age in service, the acidity and therefore the neutralization number increases. A used oil having a high neutralization number indicates that the oil is either oxidized or contaminated with materials such as varnish, paint, or other foreign matter. A basic neutralization number results from an alkaline contaminant in the oil. According to the present invention, the neutralization number is measured by ASTM D974. Preferably, the dielectric fluids of the present invention have a neutralization number of less than 0.05 mg KOH/g, more preferably less than 0.03 mg KOH/g, and even more preferably less than 0.02 mg KOH/g.

Dissipation factor of a dielectric fluid is the cosine of the phase angle between a sinusoidal potential applied to the oil and the resulting current. Dissipation factor indicates the dielectric loss of an oil; thus the dielectric heating. A high dissipation factor is an indication of the presence of contamination or deterioration products such as moisture, carbon or other conducting matter, metal soaps and products of oxidation. According to the present invention, the dissipation factor is measured by ASTM D924. Preferably, the dielectric fluids of the present invention have a dissipation factor of less than 0.05 at 25° C. and less than 0.30 at 10° C.

The boiling points of the oils derived from highly paraffinic wax of the present invention are measured by simulated distillation using ASTM D 6352 and reported in ° F. at different mass percents recovered. The Boiling Range Distribution (5-95) is calculated by subtracting the $T_5$ (5 mass percent recovered) boiling point from the $T_{95}$ (95 mass percent recovered) boiling point, in ° F.

Further specification standards used herein in the Examples include ASTM D3487, an ASTM Type II standard specification for mineral insulating oil used in electrical apparatus; ASTM D5222-00, an ASTM standard specification for high fire-point electrical insulating oil (high molecular weight hydrocarbon specification); IEEE C57.121, an Institute of Electrical and Electronic Engineers 1998 IEEE Guide for Acceptance and Maintenance of Less Flammable Hydrocarbon Fluid in Transformers; and IEC 1099, an International Electrochemical Commission Specification for Unused Synthetic Organic Esters for Electrical Purposes. If not specified, the following test methods were used in the Examples: Kinematic Viscosity, ASTM D445; Appearance @ 25° C., Visual, ASTM D1524; Interfacial Tension, ASTM D971; Neutralization Number, ASTM D974; and Boiling Range Distribution (5-95) ($T_{95}$ minus $T_5$), ASTM D6352.

Highly Paraffinic Wax

The highly paraffinic wax used in making the oil fractions of the present invention can be any wax having a high content of n-paraffins. Preferably, the highly paraffinic wax comprise greater than 40 weight % n-paraffins, preferably greater than 50 weight %, and more preferably greater than 75 weight %. Preferably, the highly paraffinic waxes used in the present invention also have very low levels of nitrogen and sulfur, generally less than 25 ppm total combined nitrogen and sulfur and preferably less than 20 ppm. Examples of highly paraffinic waxes that may be used in the present invention include slack waxes, deoiled slack waxes, refined foots oils, waxy lubricant raffinates, n-paraffin waxes, NAO waxes, waxes produced in chemical plant processes, deoiled petroleum derived waxes, microcrystalline waxes, Fischer-Tropsch waxes, and mixtures thereof. The pour points of the highly paraffinic waxes useful in this invention are greater than 50° C. and preferably greater than 60° C.

It has been discovered that these highly paraffinic waxes can be processed to provide oil fractions having high boiling points relative to their viscosities. Accordingly, these oil fractions can be used to provide dielectric fluids with high flash points, high fire points, and high dielectric breakdown. In one preferred embodiment, the highly paraffinic wax is a Fischer-Tropsch derived wax and provides a Fischer-Tropsch derived oil fraction.

Process for Providing Oil Fraction

The dielectric fluids according to the present invention comprise one or more oil fractions derived from highly paraffinic wax. The oil fractions derived from highly paraffinic wax of the present invention are prepared from the highly paraffinic wax by a process including hydroisomerization. Preferably, the highly paraffinic wax is hydroisomerized using a shape selective intermediate pore size molecular sieve comprising a noble metal hydrogenation component under conditions of about 600° F. to 750° F. The product from the hydroisomerization is fractionated to provide one or more fractions having a $T_{90}$ boiling point greater than or equal to 950° F., a kinematic viscosity between about 6 cSt and about 20 cSt, and a pour point of greater than or equal to −14° C. The oil fractions are used to provide a dielectric fluid having a dielectric breakdown of greater than or equal to 25 kV as measured by ASTM D877. The oil fractions derived from highly paraffinic wax also comprise less than 0.30 weight percent aromatics and ≧10 weight % molecules with monocycloparaffinic functionality and ≦3 weight % molecules with multicycloparaffinic functionality.

In one preferred embodiment, the highly paraffinic wax is a Fischer-Tropsch derived wax and provides a Fischer-Tropsch derived oil fraction.

These oil fractions are made by process comprising providing a highly paraffinic wax and then hydroisomerizing the highly paraffinic wax to provide an isomerized oil. The process further comprises fractionating the isomerized oil obtained from the hydroisomerization process to provide one or more fractions having a $T_{90}$ boiling point of greater than or equal to 950° F. Fractions are then selected that have the above set forth properties.

In a preferred embodiment, the oil fraction according to the present invention is a Fischer-Tropsch derived oil fraction. The Fischer-Tropsch derived oil fraction used as a dielectric fluid is made by a Fischer-Tropsch synthesis process followed by hydroisomerization of the waxy fractions of the Fischer-Tropsch syncrude.

Fischer-Tropsch Synthesis

In Fischer-Tropsch chemistry, syngas is converted to liquid hydrocarbons by contact with a Fischer-Tropsch catalyst under reactive conditions. Typically, methane and optionally heavier hydrocarbons (ethane and heavier) can be sent through a conventional syngas generator to provide synthesis gas. Generally, synthesis gas contains hydrogen and carbon monoxide, and may include minor amounts of carbon dioxide and/or water. The presence of sulfur, nitrogen, halogen, selenium, phosphorus and arsenic contaminants in the syngas is undesirable. For this reason and depending on the quality of the syngas, it is preferred to remove sulfur and other contaminants from the feed before performing the Fischer-Tropsch chemistry. Means for removing these contaminants are well known to those of skill in the art. For example, ZnO guardbeds are preferred for removing sulfur impurities. Means for removing other contaminants are well known to those of skill in the art. It also may be desirable to purify the syngas prior to the Fischer-Tropsch reactor to remove carbon dioxide produced during the syngas reaction and any additional sulfur compounds not already removed. This can be accomplished, for example, by contacting the syngas with a mildly alkaline solution (e.g., aqueous potassium carbonate) in a packed column.

In the Fischer-Tropsch process, contacting a synthesis gas comprising a mixture of $H_2$ and CO with a Fischer-Tropsch catalyst under suitable temperature and pressure reactive conditions forms liquid and gaseous hydrocarbons. The Fischer-Tropsch reaction is typically conducted at temperatures of about 300-700° F. (149-371° C.), preferably about 400-550° F. (204-228° C.); pressures of about 10-600 psia, (0.7-41 bars), preferably about 30-300 psia, (2-21 bars) and catalyst space velocities of about 100-10,000 cc/g/hr, preferably about 300-3,000 cc/g/hr. Examples of conditions for performing Fischer-Tropsch type reactions are well known to those of skill in the art.

The products of the Fischer-Tropsch synthesis process may range from $C_1$ to $C_{200+}$ with a majority in the $C_5$ to $C_{100+}$ range. The reaction can be conducted in a variety of reactor types, such as fixed bed reactors containing one or more catalyst beds, slurry reactors, fluidized bed reactors, or a combination of different type reactors. Such reaction processes and reactors are well known and documented in the literature.

The slurry Fischer-Tropsch process, which is preferred in the practice of the invention, utilizes superior heat (and mass) transfer characteristics for the strongly exothermic synthesis reaction and is able to produce relatively high molecular weight, paraffinic hydrocarbons when using a cobalt catalyst. In the slurry process, a syngas comprising a mixture of hydrogen and carbon monoxide is bubbled up as a third phase through a slurry which comprises a particulate Fischer-Tropsch type hydrocarbon synthesis catalyst dispersed and suspended in a slurry liquid comprising hydrocarbon products of the synthesis reaction which are liquid under the reaction conditions. The mole ratio of the hydrogen to the carbon monoxide may broadly range from about 0.5 to about 4, but is more typically within the range of from about 0.7 to about 2.75 and preferably from about 0.7 to about 2.5. A particularly preferred Fischer-Tropsch process is taught in EP0609079, also completely incorporated herein by reference for all purposes.

In general, Fischer-Tropsch catalysts contain a Group VIII transition metal on a metal oxide support. The catalysts may also contain a noble metal promoter(s) and/or crystalline molecular sieves. Suitable Fischer-Tropsch catalysts comprise one or more of Fe, Ni, Co, Ru and Re, with cobalt being preferred. A preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides.

In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Suitable support materials include alumina, silica, magnesia and titania or mixtures thereof. Preferred supports for cobalt containing catalysts comprise titania. Useful catalysts and their preparation are known and illustrated in U.S. Pat. No. 4,568,663, which is intended to be illustrative but non-limiting relative to catalyst selection.

Certain catalysts are known to provide chain growth probabilities that are relatively low to moderate, and the reaction products include a relatively high proportion of low molecular ($C_{2-8}$) weight olefins and a relatively low proportion of high molecular weight ($C_{30+}$) waxes. Certain other catalysts are known to provide relatively high chain growth probabilities, and the reaction products include a relatively low proportion of low molecular ($C_{2-8}$) weight olefins and a relatively high proportion of high molecular weight ($C_{30+}$) waxes. Such catalysts are well known to those of skill in the art and can be readily obtained and/or prepared.

The product from a Fischer-Tropsch process contains predominantly paraffins. The products from Fischer-Tropsch reactions generally include a light reaction product and a waxy reaction product. The light reaction product (i.e., the condensate fraction) includes hydrocarbons boiling below about 700° F. (e.g., tail gases through middle distillate fuels), largely in the $C_5$-$C_{20}$ range, with decreasing amounts up to about $C_{30}$. The waxy reaction product (i.e., the wax fraction) includes hydrocarbons boiling above about 600° F. (e.g., vacuum gas oil through heavy paraffins), largely in the $C_{20+}$ range, with decreasing amounts down to $C_{10}$. Both the light reaction product and the waxy product are substantially paraffinic. The waxy product generally comprises greater than 70 weight % normal paraffins, and often greater than 80 weight % normal paraffins. The light reaction product comprises paraffinic products with a significant proportion of alcohols and olefins. In some cases, the light reaction product may comprise as much as 50 weight %, and even higher, alcohols and olefins. It is the waxy reaction product (i.e., the wax fraction) that is used as a feedstock to the process for providing the Fischer-Tropsch derived oil fractions used as a dielectric fluid according to the present invention.

The Fischer-Tropsch wax useful in this invention has a weight ratio of products of carbon number 60 or greater to products of carbon number 30 or greater of less than 0.18. The weight ratio of products of carbon number 60 or greater to products of carbon number 30 or greater is determined as follows: 1) measuring the boiling point distribution of the Fischer-Tropsch wax by simulated distillation using ASTM D 6352; 2) converting the boiling points to percent weight distribution by carbon number, using the boiling points of n-paraffins published in Table 1 of ASTM D 6352-98; 3) summing the weight percents of products of carbon number 30 or greater; 4) summing the weight percents of products of carbon number 60 or greater; and 5) dividing the sum of weight percents of products of carbon number 60 or greater by the sum of weight percents of products of carbon number 30 or greater. Other embodiments of this invention use Fischer-Tropsch wax having a weight ratio of products of carbon number 60 or greater to products of carbon number 30 or greater of less than 0.15, and preferably of less than 0.10.

The Fischer-Tropsch oil fractions used to provide a dielectric fluid are prepared from the waxy fractions of the Fischer-Tropsch syncrude by a process including hydroisomerization. The Fischer-Tropsch oil fractions may be made by a process as described in U.S. Ser. No. 10/744,870, filed Dec. 23, 2003, herein incorporated by reference in its entirety. The Fischer-Tropsch oil fractions used to provide a dielectric fluid according to the present invention may be manufactured at a site different from the site at which the other optional components of the dielectric fluid are received and blended.

Hydroisomerization

The highly paraffinic waxes are subjected to a process comprising hydroisomerization to provide the oil fractions useful as a dielectric fluid according to the present invention.

Hydroisomerization is intended to improve the cold flow properties of the oil by the selective addition of branching into the molecular structure. Hydroisomerization ideally will achieve high conversion levels of the highly paraffinic wax to non-waxy iso-paraffins while at the same time minimizing the conversion by cracking. Preferably, the conditions for hydroisomerization in the present invention are controlled such that the conversion of the compounds boiling above about 700° F. in the wax feed to compounds boiling below about 700° F. is maintained between about 10 wt % and 50 wt %, preferably between 15 wt % and 45 wt %.

According to the present invention, hydroisomerization is conducted using a shape selective intermediate pore size molecular sieve. Hydroisomerization catalysts useful in the present invention comprise a shape selective intermediate pore size molecular sieve and optionally a catalytically active metal hydrogenation component on a refractory oxide support. The phrase "intermediate pore size," as used herein means an effective pore aperture in the range of from about 3.9 to about 7.1 Å when the porous inorganic oxide is in the calcined form. The shape selective intermediate pore size molecular sieves used in the practice of the present invention are generally 1-D 10-, 11- or 12-ring molecular sieves. The preferred molecular sieves of the invention are of the 1-D 10-ring variety, where 10-(or 11-or 12-) ring molecular sieves have 10 (or 11 or 12) tetrahedrally-coordinated atoms (T-atoms) joined by oxygens. In the 1-D molecular sieve, the 10-ring (or larger) pores are parallel with each other, and do not interconnect. Note, however, that 1-D 10-ring molecular sieves which meet the broader definition of the intermediate pore size molecular sieve but include intersecting pores having 8-membered rings may also be encompassed within the definition of the molecular sieve of the present invention. The classification of intrazeolite channels as 1-D, 2-D and 3-D is set forth by R. M. Barrer in Zeolites, Science and Technology, edited by F. R. Rodrigues, L. D. Rollman and C. Naccache, NATO ASI Series, 1984 which classification is incorporated in its entirety by reference (see particularly page 75).

Preferred shape selective intermediate pore size molecular sieves used for hydroisomerization are based upon aluminum phosphates, such as SAPO-11, SAPO-31, and SAPO-41. SAPO-11 and SAPO-31 are more preferred, with SAPO-11 being most preferred. SM-3 is a particularly preferred shape selective intermediate pore size SAPO, which has a crystalline structure falling within that of the SAPO-11 molecular sieves. The preparation of SM-3 and its unique characteristics are described in U.S. Pat. Nos. 4,943,424 and 5,158,665. Also preferred shape selective intermediate pore size molecular sieves used for hydroisomerization are zeolites, such as ZSM-22, ZSM-23, ZSM-35, ZSM-48, ZSM-57, SSZ-32, offretite, and ferrierite. SSZ-32 and ZSM-23 are more preferred.

A preferred intermediate pore size molecular sieve is characterized by selected crystallographic free diameters of the channels, selected crystallite size (corresponding to selected channel length), and selected acidity. Desirable crystallographic free diameters of the channels of the molecular sieves are in the range of from about 3.9 to about 7.1 Angstrom, having a maximum crystallographic free diameter of not more than 7.1 and a minimum crystallographic free diameter of not less than 3.9 Angstrom. Preferably the maximum crystallographic free diameter is not more than 7.1 and the minimum crystallographic free diameter is not less than 4.0 Angstrom. Most preferably the maximum crystallographic free diameter is not more than 6.5 and the minimum crystallographic free diameter is not less than 4.0 Angstrom. The crystallographic free diameters of the channels of molecular sieves are published in the "Atlas of Zeolite Framework Types", Fifth Revised Edition, 2001, by Ch. Baerlocher, W. M. Meier, and D. H. Olson, Elsevier, pp 10-15, which is incorporated herein by reference.

A particularly preferred intermediate pore size molecular sieve, which is useful in the present process is described, for example, in U.S. Pat. Nos. 5,135,638 and 5,282,958, the contents of which are hereby incorporated by reference in their entirety. In U.S. Pat. No. 5,282,958, such an intermediate pore size molecular sieve has a crystallite size of no more than about 0.5 microns and pores with a minimum diameter of at least about 4.8 Å and with a maximum diameter of about 7.1 Å. The catalyst has sufficient acidity so that 0.5 grams thereof when positioned in a tube reactor converts at least 50% of hexadecane at 370° C., a pressure of 1200 psig, a hydrogen flow of 160 ml/min, and a feed rate of 1 ml/hr. The catalyst also exhibits isomerization selectivity of 40 percent or greater (isomerization selectivity is determined as follows: 100×(weight % branched $C_{16}$ in product)/(weight % branched $C_{16}$ in product+weight % $C_{13-}$ in product) when used under conditions leading to 96% conversion of normal hexadecane (n-$C_{16}$) to other species.

Such a particularly preferred molecular sieve may further be characterized by pores or channels having a crystallographic free diameter in the range of from about 4.0 to about 7.1 Å, and preferably in the range of 4.0 to 6.5 Å. The crystallographic free diameters of the channels of molecular sieves are published in the "Atlas of Zeolite Framework Types", Fifth Revised Edition, 2001, by Ch. Baerlocher, W. M. Meier, and D. H. Olson, Elsevier, pp 10-15, which is incorporated herein by reference.

If the crystallographic free diameters of the channels of a molecular sieve are unknown, the effective pore size of the molecular sieve can be measured using standard adsorption techniques and hydrocarbonaceous compounds of known minimum kinetic diameters. See Breck, Zeolite Molecular Sieves, 1974 (especially Chapter 8); Anderson et al. J. Catalysis 58, 114 (1979); and U.S. Pat. No. 4,440,871, the pertinent portions of which are incorporated herein by reference. In performing adsorption measurements to determine pore size, standard techniques are used. It is convenient to consider a particular molecule as excluded if does not reach at least 95% of its equilibrium adsorption value on the molecular sieve in less than about 10 minutes ($p/p_o$=0.5 at 25° C.). Intermediate pore size molecular sieves will typically admit molecules having kinetic diameters of 5.3 to 6.5 Angstrom with little hindrance.

Hydroisomerization catalysts useful in the present invention comprise a catalytically active hydrogenation metal. The presence of a catalytically active hydrogenation metal leads to product improvement, especially VI and stability. Typical catalytically active hydrogenation metals include chromium, molybdenum, nickel, vanadium, cobalt, tungsten, zinc, platinum, and palladium. The metals platinum and palladium are especially preferred, with platinum most especially preferred. If platinum and/or palladium is used, the total amount of active hydrogenation metal is typically in the range of 0.1 to 5 weight percent of the total catalyst, usually from 0.1 to 2 weight percent, and not to exceed 10 weight percent.

The refractory oxide support may be selected from those oxide supports, which are conventionally used for catalysts, including silica, alumina, silica-alumina, magnesia, titania, and combinations thereof.

The conditions for hydroisomerization will be tailored to achieve an oil fraction comprising less than about 0.3 weight % aromatics, greater than or equal to 10 weight % molecules with monocycloparaffinic functionality, and less than or equal to 3 weight % molecules with multicycloparaffinic functionality. Preferably, the conditions provide an oil fraction comprising greater than 15 weight % molecules with monocycloparaffinic functionality and less than or equal to 2.5 weight % molecules with multicycloparaffinic functionality and more preferably less than or equal to 1.5 weight % molecules with multicycloparaffinic functionality. Preferably, the conditions provide an oil fraction having a ratio of weight percent of molecules with monocycloparaffinic functionality of weight percent of molecules with multicycloparaffinic functionality of greater than 5, more preferably greater than 15, and even more preferably greater than 50. The conditions for hydroisomerization will also be tailored to achieve an oil fraction as described above having a $T_{90}$ boiling point of greater than or equal to 950° F., a kinematic viscosity of between about 6 cSt and about 20 cSt at 100° C., a pour point of greater than or equal to −14° C. The oil fraction will be used to provide a dielectric fluid having a dielectric breakdown of greater than or equal to 25 kV as measured by ASTM D877.

The conditions for hydroisomerization will depend on the properties of feed used, the catalyst used, whether or not the catalyst is sulfided, the desired yield, and the desired properties of the oil. Conditions under which the hydroisomerization process of the current invention may be carried out include temperatures from about 500° F. to about 775° F. (260° C. to about 413° C.), preferably 600° F. to about 750° F. (315° C. to about 399° C.), more preferably about 600° F. to about 700° F. (315° C. to about 371° C.); and pressures from about 15 to 3000 psig, preferably 100 to 2500 psig. The hydroisomerization pressures in this context refer to the hydrogen partial pressure within the hydroisomerization reactor, although the hydrogen partial pressure is substantially the same (or nearly the same) as the total pressure. The liquid hourly space velocity during contacting is generally from about 0.1 to 20 hr-1, preferably from about 0.1 to about 5 hr-1. The hydrogen to hydrocarbon ratio falls within a range from about 1.0 to about 50 moles $H_2$ per mole hydrocarbon, more preferably from about 10 to about 20 moles $H_2$ per mole hydrocarbon. Suitable conditions for performing hydroisomerization are described in U.S. Pat. Nos. 5,282,958 and 5,135,638, the contents of which are incorporated by reference in their entirety.

Hydrogen is present in the reaction zone during the hydroisomerization process, typically in a hydrogen to feed ratio from about 0.5 to 30 MSCF/bbl (thousand standard cubic feet per barrel), preferably from about 1 to about 10 MSCF/bbl. Hydrogen may be separated from the product and recycled to the reaction zone.

Fractionation

The process to provide the oil fractions derived from highly paraffinic wax optionally include fractionating the highly paraffinic wax feed prior to hydroisomerization.

The process to provide the oil fractions derived from highly paraffinic wax includes fractionating of the oil obtained from the hydroisomerization process to provide one or more oil fractions having a $T_{90}$ boiling point of greater than or equal to 950° F. The fractionation of the highly paraffinic wax feed or the isomerized oil into fractions is generally accomplished by either atmospheric or vacuum distillation, or by a combination of atmospheric and vacuum distillation. Atmospheric distillation is typically used to separate the lighter distillate fractions, such as naphtha and middle distillates, from a bottoms fraction having an initial boiling point above about 600° F. to about 750° F. (about 315° C. to about 399° C.). At higher temperatures thermal cracking of the hydrocarbons may take place leading to fouling of the equipment and to lower yields of the heavier cuts. Vacuum distillation is typically used to separate the higher boiling material, such as the oil fractions, into different boiling range cuts.

Fractionating the isomerized oil into different boiling range cuts enables an oil fraction with the properties as set forth herein to be obtained. Accordingly, the isomerized oil is fractionated to provide one or more fractions having a $T_{90}$ boiling point of greater than or equal to 950° F. The fractions obtained from the isomerized oil, having a $T_{90}$ boiling point of greater than or equal to 950° F., also have a fairly wide Boiling Range Distribution (5-95). The Boiling Range Distributions (5-95) of the fractions obtained from the isomerized oil, having a $T_{90}$ boiling point of greater than or equal to 950° F., may be greater than about 125° F., in certain embodiments greater than about 150° F., and in some embodiments greater than about 200° F.

The insulating dielectric fluid of the present invention may comprise one or more fractions obtained from the isomerized oil, having a $T_{90}$ boiling point of greater than or equal to 950° F. When the insulating dielectric fluid of the present invention comprises at least two fractions obtained from the isomerized oil, having a $T_{90}$ boiling point of greater than or equal to 950° F., the Boiling Range Distribution (5-95) of the oil fractions will generally be greater than about 200° F.

Desired fractions are selected to provide a dielectric fluid having dielectric breakdown by ASTM D 877 greater than about 25 kV, preferably greater than about 30 kV, more preferably greater than about 40 kV.

Hydrotreating

The highly paraffinic waxy feed to the hydroisomerization process may be hydrotreated prior to hydroisomerization. Hydrotreating refers to a catalytic process, usually carried out in the presence of free hydrogen, in which the primary purpose is the removal of various metal contaminants, such as arsenic, aluminum, and cobalt; heteroatoms, such as sulfur and nitrogen; oxygenates; or aromatics from the feed stock. Generally, in hydrotreating operations cracking of the hydrocarbon molecules, i.e., breaking the larger hydrocarbon molecules into smaller hydrocarbon molecules, is minimized, and the unsaturated hydrocarbons are either fully or partially hydrogenated.

Catalysts used in carrying out hydrotreating operations are well known in the art. See, for example, U.S. Pat. Nos. 4,347,121 and 4,810,357, the contents of which are hereby incorporated by reference in their entirety, for general descriptions of hydrotreating, hydrocracking, and of typical catalysts used in each of the processes. Suitable catalysts include noble metals from Group VIIIA (according to the 1975 rules of the International Union of Pure and Applied Chemistry), such as platinum or palladium on an alumina or siliceous matrix, and Group VIII and Group VIB, such as nickel-molybdenum or nickel-tin on an alumina or siliceous matrix. U.S. Pat. No. 3,852,207 describes a suitable noble metal catalyst and mild conditions. Other suitable catalysts are described, for example, in U.S. Pat. Nos. 4,157,294 and 3,904,513. The non-noble hydrogenation metals, such as nickel-molybdenum, are usually present in the final catalyst composition as oxides, but are usually employed in their reduced or sulfided forms when such sulfide compounds are readily formed from the particular metal involved. Preferred non-noble metal catalyst compositions contain in excess of about 5 weight percent, preferably about 5 to about 40 weight percent molybdenum and/or tungsten, and at least about 0.5, and generally about 1 to about 15 weight percent of nickel and/or cobalt determined as the corresponding oxides. Catalysts containing noble metals, such as platinum, contain in excess of 0.01 percent metal, preferably between 0.1 and 1.0 percent metal. Combinations of noble metals may also be used, such as mixtures of platinum and palladium.

Typical hydrotreating conditions vary over a wide range. In general, the overall LHSV is about 0.25 to 2.0, preferably about 0.5 to 1.5. The hydrogen partial pressure is greater than 200 psia, preferably ranging from about 500 psia to about 2000 psia. Hydrogen recirculation rates are typically greater than 50 SCF/Bbl, and are preferably between 1000 and 5000 SCF/Bbl. Temperatures in the reactor will range from about 300° F. to about 750° F. (about 150° C. to about 400° C.), preferably ranging from 450° F. to 725° F. (230° C. to 385° C.).

Hydrofinishing

Hydrofinishing is a hydrotreating process that may be used as a step following hydroisomerization to provide the oil fractions derived from highly paraffinic wax. Hydrofinishing is intended to improve oxidation stability, UV stability, and appearance of the oil fractions by removing traces of aromatics, olefins, color bodies, and solvents. As used in this disclosure, the term UV stability refers to the stability of the oil fraction or the dielectric fluid when exposed to UV light and oxygen. Instability is indicated when a visible precipitate forms, usually seen as flog or cloudiness, or a darker color develops upon exposure to ultraviolet light and air. A general description of hydrofinishing may be found in U.S. Pat. Nos. 3,852,207 and 4,673,487.

The oil fractions derived from highly paraffinic wax of the present invention may be hydrofinished to improve product quality and stability. During hydrofinishing, overall liquid hourly space velocity (LHSV) is about 0.25 to 2.0 $hr^{-1}$, preferably about 0.5 to 1.0 $hr^{-1}$. The hydrogen partial pressure is greater than 200 psia, preferably ranging from about 500 psia to about 2000 psia. Hydrogen recirculation rates are typically greater than 50 SCF/Bbl, and are preferably between 1000 and 5000 SCF/Bbl. Temperatures range from about 300° F. to about 750° F., preferably ranging from 450° F. to 600° F.

Suitable hydrofinishing catalysts include noble metals from Group VIIIA (according to the 1975 rules of the International Union of Pure and Applied Chemistry), such as platinum or palladium on an alumina or siliceous matrix, and unsulfided Group VIIIA and Group VIB, such as nickel-molybdenum or nickel-tin on an alumina or siliceous matrix. U.S. Pat. No. 3,852,207 describes a suitable noble metal catalyst and mild conditions. Other suitable catalysts are described, for example, in U.S. Pat. Nos. 4,157,294 and 3,904,513. The non-noble metal (such as nickel-molybdenum and/or tungsten, and at least about 0.5, and generally about 1 to about 15 weight percent of nickel and/or cobalt determined as the corresponding oxides. The noble metal (such as platinum) catalyst contains in excess of 0.01 percent metal, preferably between 0.1 and 1.0 percent metal. Combinations of noble metals may also be used, such as mixtures of platinum and palladium.

Clay treating to remove impurities, as described below, is an alternative final process step to provide oil fractions derived from highly paraffinic wax.

Aftertreating

The process to make the oil fractions derived from highly paraffinic wax may also include an aftertreating step following the hydroisomerization process. Aftertreating of the selected fractions of isomerized wax with a sorbent optionally may be used to lower the pour point, reduce the haziness, and further reduce the wax content of the treated fractions. Processes using a sorbent to reduce haziness are described in U.S. Pat. Nos. 6,579,441 and 6,468,417, the contents of which are incorporated herein by reference in their entirety. Processes using a sorbent to reduce pour point are described in EP 105631 and EP278693.

Sorbents useful for aftertreating are generally solid particulate matter having high sorptive capacity. Crystalline molecular sieves (including aluminosilicate zeolites), activated carbon, aluminas, silica-alumina and clays, are examples of useful sorbents. The sorbents most useful for reducing haziness have a surface having some acidic character.

Solvent Dewaxing

The process to make the oil fractions derived from highly paraffinic wax may also include a solvent dewaxing step following the hydroisomerization process. Solvent dewaxing optionally may be used to remove small amounts of remaining waxy molecules from the oil after hydroisomerization. Solvent dewaxing is done by dissolving the oil in a solvent, such as methyl ethyl ketone, methyl iso-butyl ketone, or toluene, or precipitating the wax molecules as discussed in Chemical Technology of Petroleum, 3rd Edition, William Gruse and Donald Stevens, McGraw-Hill Book Company, Inc., New York, 1960, pages 566 to 570. Solvent dewaxing is also described in U.S. Pat. Nos. 4,477,333, 3,773,650 and 3,775,288.

Dielectric Fluid

The dielectric fluid according to the present invention comprises one or more oil fractions derived from highly paraffinic wax with a high boiling point relative to the viscosity range, a relatively high weight percent of molecules with monocycloparaffinic functionality and a relatively low weight percent of molecules with multicycloparaffinic functionality, and a moderately low pour point. The insulating dielectric fluids of the present invention have a high dielectric breakdown. The oil fractions according to the present invention have certain properties that provide advantages for their use to provide dielectric fluids. These properties include their high boiling point relative to the viscosity range, which provides better electrical resistance and lower flash and fire points. In addition, their relatively high weight percent of molecules with monocycloparaffinic functionality provides good solvency, good seal compatibility, and miscibility with other oils. Furthermore, their relatively low weight percent of molecules with multicycloparaffinic functionality provides excellent oxidation stability. Moreover, their moderately low pour point allows a higher yield of oil, without requiring excessive yield losses due to heavy dewaxing.

Preferred embodiments of the dielectric fluids of the present invention also have very high flash and fire points, making the dielectric fluids according to the present invention useful as high fire point insulating dielectric fluids. The oil fractions are very responsive to small amounts of additives, including pour point depressants, antioxidants, and metal deactivators.

The dielectric fluids according to the present invention comprise one or more oil fractions derived from highly paraffinic wax. As such, the dielectric fluids according to the present invention comprise oil fractions derived from highly paraffinic wax having a viscosity of between about 6 cSt and 20 cSt at 100° C., a $T_{90}$ boiling point of greater than or equal to 950° C., and a pour point of greater than or equal to −14° C. In preferred embodiments, the oil fractions have a $T_{90}$ boiling point of greater than or equal to 1000° C.

The dielectric fluids according to the present invention have a dielectric breakdown of greater than or equal to 25 kV as measured by ASTM 877. In preferred embodiments, the dielectric fluids according to the present invention have a dielectric breakdown of greater than or equal to 30 kV, and more preferably greater than or equal to 40 kV as measured by ASTM 877. The dielectric fluids according to the present invention exhibit excellent dielectric breakdown and high flash and fire points. In preferred embodiments, the dielectric fluids according to the present invention have a fire point of ≧310° C., more preferably a fire point of ≧325° C., and have a flash point of ≧280° C.

The high boiling points of the oil fractions relative to their viscosities provide them with high flash points and high fire points compared to other paraffinic oils of similar viscosities. Even though the oil fractions of the present invention have high boiling points, they still flow well enough to provide effective cooling.

These fractions having a $T_{90}$ boiling point of greater than or equal to 950° F. may also have a fairly wide Boiling Range Distribution (5-95). The Boiling Range Distributions (5-95) of the fractions having a $T_{90}$ boiling point of greater than or equal to 950° F. may be greater than about 125° F., in certain embodiments greater than about 150° F., and in some embodiments greater than about 200° F.

The oil fractions derived from highly paraffinic wax comprise less than 0.30 weight percent aromatics and ≧10 weight % molecules with monocycloparaffinic functionality and ≦3 weight % molecules with multicycloparaffinic functionality. The oil fractions according to the present invention comprise extremely low levels of unsaturates. According to the present invention, the dielectric fluids comprise one or more oil fractions derived from highly paraffinic wax containing a relatively high weight percent of molecules with monocycloparaffinic functionality and a relatively low weight percent of molecules with multicycloparaffinic functionality and aromatics.

In a preferred embodiment, the oil fraction derived from highly paraffinic wax comprises ≧15 weight molecules with monocycloparaffinic functionality. In another preferred embodiment, the oil fraction derived from highly paraffinic wax comprises ≦2.5 weight percent molecules with multicycloparaffinic functionality. In another preferred embodiment, the oil fraction derived from highly paraffinic wax comprises ≦1.5 weight percent molecules with multicycloparaffinic functionality. In yet another preferred embodiment, the oil fraction derived from highly paraffinic wax comprises a ratio of weight percent of molecules with monocycloparaffinic functionality to weight percent of molecules with multicycloparaffinic functionality of greater than 5, preferably greater than 15, and more preferably greater than 50.

The high amounts of monocycloparaffinic functionality provide the oil fractions of the present invention with good solvency, good seal compatibility, and good miscibility with other oils. The very low amounts of multicycloparaffinic functionality provide the oil fractions of the present invention with excellent oxidation stability.

The pour points of the oil fractions used as dielectric fluids are −14° C. and higher, preferably −12° C. and higher. Oil fractions with these moderately low pour points can be made in abundance without the yield loss that occurs with heavy dewaxing necessary to produce oils of lower viscosity and lower pour points. According, the oil fractions used as dielectric fluids can be made in large quantities and marketed at attractive prices due to the moderately low pour point. In addition, the oil fractions of this invention respond well to additives, including pour point depressants; therefore, the pour point of the oil fractions readily can be lowered through the use of a pour point depressant additive when much lower pour points are required.

The dielectric fluids of the present invention are useful as insulating and cooling mediums in new and existing power and distribution electrical apparatus, such as transformers, regulators, circuit breakers, switchgear, underground electrical cables, and attendant equipment. They are functionally miscible with existing mineral oil based dielectric fluids and are compatible with existing apparatus. These dielectric fluids of the present invention can be used in applications requiring high flash point, high fire point, excellent dielectric breakdown, and good additive solubility. In particular, the dielectric fluids of the present invention can be used in applications in which a high fire point insulating oil is required. In addition, the oil fractions derived from highly paraffinic wax, and thus the dielectric fluids comprising these fractions, exhibit excellent oxidation resistance and good elastomer compatibility.

One embodiment of the insulating dielectric fluids of this invention are useful as dielectric and cooling mediums in new and existing power and distribution electrical apparatus, such as transformers and switchgears, where high fire point insulating oil is required. High fire point insulating oil differs from conventional insulating oil by possessing a fire point of at least 300° C. This high fire point property is necessary in order to comply with certain application requirements of the National electrical Code (Article 450-23) or other agencies. Two examples of specifications for high fire point insulating oils are IEEE Std C57.121-1988 and ASTM D 5222-00. The fire points of the insulating dielectric fluids of this invention will generally be greater than about 250° C., preferably greater than about 300° C., more preferably greater than about 310° C., most preferably greater than about 325° C. The insulating dielectric fluid of this invention useful as high fire point insulating oil will generally have a fire point between about 300° C. and about 350° C. In addition to having a high fire point, high fire point insulating oil must also possess a flash point of at least 275° C. The flash points of the insulating dielectric fluids of this invention are generally greater than about 150° C., preferably greater than about 280° C., more preferably greater than about 290° C.

In another embodiment, the insulating dielectric fluids of this invention are useful as dielectric and insulating fluids in underground electrical cables. The insulating dielectric fluid, in addition to electrical insulation in this case, penetrates the surfaces of the underground electrical cable to remove any moisture and also to prevent future moisture from entering the cable.

The oil fractions of the present invention used as dielectric fluids contain greater than 95 weight % saturates as determined by elution column chromatography, ASTM D 2549-02. Olefins are present in an amount less than detectable by long duration $C^{13}$ Nuclear Magnetic Resonance Spectroscopy (NMR). Preferably, molecules with aromatic functionality are present in amounts less than 0.3 weight percent by HPLC-UV, and confirmed by ASTM D 5292-99 modified to measure low level aromatics. In preferred embodiments molecules with aromatic functionality are present in amounts less than 0.10 weight percent, preferably less than 0.05 weight percent, more preferably less than 0.01 weight percent. Sulfur is present in amounts less than 25 ppm, preferably less than 5 ppm, and more preferably less than 1 ppm as determined by ultraviolet fluorescence by ASTM D 5453-00.

The oil fractions do not introduce any undesirable characteristics, including, for example, high volatility and impurities such as heteroatoms, to the dielectric fluid.

In a preferred embodiment, the oil fraction according to the present invention is a Fischer-Tropsch derived oil fraction. Fischer-Tropsch derived waxes are particularly well suited for providing Fischer-Tropsch derived oil fractions with the above-described properties.

Aromatics Measurement by HPLC-UV:

The method used to measure low levels of molecules with aromatic functionality in the oils uses a Hewlett Packard 1050 Series Quaternary Gradient High Performance Liquid Chromatography (HPLC) system coupled with a HP 1050 Diode-Array UV-Vis detector interfaced to an HP Chemstation. Identification of the individual aromatic classes in the highly saturated oils was made on the basis of their UV spectral pattern and their elution time. The amino column used for this analysis differentiates aromatic molecules largely on the basis of their ring-number (or more correctly, double-bond number). Thus, the single ring aromatic containing molecules would elute first, followed by the polycyclic aromatics in order of increasing double bond number per molecule. For aromatics with similar double bond character, those with only alkyl substitution on the ring would elute sooner than those with cycloparaffinic substitution.

Unequivocal identification of the various oil aromatic hydrocarbons from their UV absorbance spectra was somewhat complicated by the fact their peak electronic transitions were all red-shifted relative to the pure model compound analogs to a degree dependent on the amount of alkyl and cycloparaffinic substitution on the ring system. These bathochromic shifts are well known to be caused by alkyl-group delocalization of the π-electrons in the aromatic ring. Since few unsubstituted aromatic compounds boil in the oil range, some degree of red-shift was expected and observed for all of the principle aromatic groups identified.

Quantification of the eluting aromatic compounds was made by integrating chromatograms made from wavelengths optimized for each general class of compounds over the appropriate retention time window for that aromatic. Retention time window limits for each aromatic class were determined by manually evaluating the individual absorbance spectra of eluting compounds at different times and assigning them to the appropriate aromatic class based on their qualitative similarity to model compound absorption spectra. With few exceptions, only five classes of aromatic compounds were observed in highly saturated API Group II and III lubricant base oils.

HPLC-UV Calibration:

HPLC-UV is used for identifying these classes of aromatic compounds even at very low levels. Multi-ring aromatics typically absorb 10 to 200 times more strongly than single-ring aromatics. Alkyl-substitution also affected absorption by about 20%. Therefore, it is important to use HPLC to separate and identify the various species of aromatics and know how efficiently they absorb.

Five classes of aromatic compounds were identified. With the exception of a small overlap between the most highly retained alkyl-cycloalkyl-1-ring aromatics and the least highly retained alkyl naphthalenes, all of the aromatic compound classes were baseline resolved. Integration limits for the co-eluting 1-ring and 2-ring aromatics at 272 nm were made by the perpendicular drop method. Wavelength dependent response factors for each general aromatic class were first determined by constructing Beer's Law plots from pure model compound mixtures based on the nearest spectral peak absorbances to the substituted aromatic analogs.

For example, alkyl-cyclohexylbenzene molecules in oils exhibit a distinct peak absorbance at 272 nm that corresponds to the same (forbidden) transition that unsubstituted tetralin model compounds do at 268 nm. The concentration of alkyl-cycloalkyl-1-ring aromatics in oil samples was calculated by assuming that its molar absorptivity response factor at 272 nm was approximately equal to tetralin's molar absorptivity at 268 nm, calculated from Beer's law plots. Weight percent concentrations of aromatics were calculated by assuming that the average molecular weight for each aromatic class was approximately equal to the average molecular weight for the whole oil sample.

This calibration method was further improved by isolating the 1-ring aromatics directly from the oils via exhaustive HPLC chromatography. Calibrating directly with these aromatics eliminated the assumptions and uncertainties associated with the model compounds. As expected, the isolated aromatic sample had a lower response factor than the model compound because it was more highly substituted.

More specifically, to accurately calibrate the HPLC-UV method, the substituted benzene aromatics were separated from the bulk of the oil using a Waters semi-preparative HPLC unit. 10 grams of sample was diluted 1:1 in n-hexane and injected onto an amino-bonded silica column, a 5 cm×22.4 mm ID guard, followed by two 25 cm×22.4 mm ID columns of 8-12 micron amino-bonded silica particles, manufactured by Rainin Instruments, Emeryville, Calif., with n-hexane as the mobile phase at a flow rate of 18 mls/min. Column eluent was fractionated based on the detector response from a dual wavelength UV detector set at 265 nm and 295 nm. Saturate fractions were collected until the 265 nm absorbance showed a change of 0.01 absorbance units, which signaled the onset of single ring aromatic elution. A single ring aromatic fraction was collected until the absorbance ratio between 265 nm and 295 nm decreased to 2.0, indicating the onset of two ring aromatic elution. Purification and separation of the single ring aromatic fraction was made by re-chromatographing the monoaromatic fraction away from the "tailing" saturates fraction which resulted from overloading the HPLC column.

This purified aromatic "standard" showed that alkyl substitution decreased the molar absorptivity response factor by about 20% relative to unsubstituted tetralin.

Confirmation of Aromatics by NMR:

The weight percent of molecules with aromatic functionality in the purified mono-aromatic standard was confirmed via long-duration carbon 13 NMR analysis. NMR was easier to calibrate than HPLC UV because it simply measured aromatic carbon so the response did not depend on the class of aromatics being analyzed. The NMR results were translated from % aromatic carbon to % aromatic molecules (to be consistent with HPLC-UV and D 2007) by knowing that 95-99% of the aromatics in highly saturated oils were single-ring aromatics.

High power, long duration, and good baseline analysis were needed to accurately measure aromatics down to 0.2% aromatic molecules.

More specifically, to accurately measure low levels of all molecules with at least one aromatic function by NMR, the standard D 5292-99 method was modified to give a minimum carbon sensitivity of 500:1 (by ASTM standard practice E 386). A15-hour duration run on a 400-500 MHz NMR with a 10-12 mm Nalorac probe was used. Acorn PC integration software was used to define the shape of the baseline and consistently integrate. The carrier frequency was changed once during the run to avoid artifacts from imaging the aliphatic peak into the aromatic region. By taking spectra on either side of the carrier spectra, the resolution was improved significantly.

Determination of Weight Percent Olefins:

The weight percent of olefins was determined by Proton-NMR (PROTON NMR) as set forth in the following steps, A-D:

a) Prepare a solution of 5-10 weight % of the test hydrocarbon in deuterochloroform.

b) Acquire a normal proton spectrum of at least 12 ppm spectral width and accurately reference the chemical shift (ppm) axis. The instrument used must have sufficient gain range to acquire a signal without overloading the receiver/ADC. When a 30 degree pulse is applied, the instrument must have a minimum signal digitization dynamic range of 65,000. Preferably the dynamic range will be 260,000 or more.

c) Measure the integral intensities between 6.0-4.5 ppm (olefin); 2.2-1.9 ppm (allylic); and 1.9-0.5 ppm (saturate)

d) Using the molecular weight of the test substance determined by ASTM D 2502 or ASTM D 2503, calculate the following:

1) The average molecular formula of the saturated hydrocarbons;
2) The average molecular formula of the olefins;
3) The total integral intensity (=sum of all integral intensities);
4) The integral intensity per sample hydrogen (=total integral/number of hydrogens in formula);
5) The number of olefin hydrogens (=Olefin integral/integral per hydrogen);
6) The number of double bonds (=Olefin hydrogen times hydrogens in olefin formula/2); and
7) The weight % of olefins by PROTON NMR=100 times the number of double bonds times the number of hydrogens in a typical olefin molecule divided by the number of hydrogens in a typical test substance molecule.

The weight percent olefins by PROTON NMR calculation procedure as set forth is step d) works best when the resulting weight percent of olefins is low, less than about 15 weight percent. The olefins must be "conventional" olefins; i.e. a distributed mixture of those olefin types having hydrogens attached to the double bond carbons such as: alpha, vinylidene, cis, trans, and trisubstituted. These olefin types will have a detectable allylic to olefin integral ratio between 1 and about 2.5. When this ratio exceeds about 3, it indicates a higher percentage of tri or tetra substituted olefins are present and that different assumptions must be made to calculate the number of double bonds in the sample.

Cycloparaffin Distribution by FIMS:

Paraffins are considered more stable than cycloparaffins towards oxidation, and therefore, more desirable. Monocycloparaffins are considered more stable than multicycloparaffins towards oxidation. However, when the weight percent of all molecules with at least one cycloparaffinic function is very low in an oil, the additive solubility is low and the elastomer compatibility is poor. Examples of oils with these properties are Fischer-Tropsch oils (GTL oils) with less than about 5% cycloparaffins. To improve these properties in finished products, expensive co-solvents such as esters must often be added. Preferably, the oil fractions, derived from highly paraffinic wax and used as dielectric fluids, comprise a high weight percent of molecules with monocycloparaffinic functionality and a low weight percent of molecules with multicycloparaffinic functionality such that the oil fractions have high oxidation stability, low volatility, good miscibility with other oils, good additive solubility, and good elastomer compatibility.

The lubricant base oils of this invention were characterized by FIMS into alkanes and molecules with different numbers of unsaturations. The distribution of molecules in the oil fractions was determined by field ionization mass spectroscopy (FIMS). FIMS spectra were obtained on a Micromass VG 70VSE mass spectrometer. The samples were introduced via a solid probe into the spectrophotometer, preferably by placing a small amount (about 0.1 mg) of the base oil to be tested in a glass capillary tube. The capillary tube was placed at the tip of a solids probe for a mass spectrometer, and the probe was heated from about 40° C. up to 500° C. at a rate of 50° C. per minute, operating under vacuum at approximately $10^{-6}$ Torr. The mass spectrometer was scanned from m/z 40 to m/z 1000 at a rate of 5 seconds per decade. The acquired mass spectra were summed to generate one "averaged" spectrum. Each spectrum was $^{13}C$ corrected using a software package from PC-MassSpec.

Response factors for all compound types were assumed to be 1.0, such that weight percent was determined from area percent. The acquired mass spectra were summed to generate one "averaged" spectrum. The output from the FIMS analysis is the average weight percents of alkanes, 1-unsaturations, 2-unsaturations, 3-unsaturations, 4-unsaturations, 5-unsaturations, and 6-unsaturations in the test sample.

The molecules with different numbers of unsaturations may be comprised of cycloparaffins, olefins, and aromatics. If aromatics were present in significant amounts in the lubricant base oil they would most likely be identified in the FIMS analysis as 4-unsaturations. When olefins were present in significant amounts in the lubricant base oil they would most likely be identified in the FIMS analysis as 1-unsaturations. The total of the 1-unsaturations, 2-unsaturations, 3-unsaturations, 4-unsaturations, 5-unsaturations, and 6-unsaturations from the FIMS analysis, minus the weight percent of olefins by proton NMR, and minus the weight percent of aromatics by HPLC-UV is the total weight percent of molecules with cycloparaffin functionality in the lubricant base oils of this invention. The total of the 2-unsaturations, 3-unsaturations, 4-unsaturations, 5-unsaturations, and 6-unsaturations from the FIMS analysis, minus the weight percent of aromatics by HPLC-UV is the weight percent of molecules with multicycloparaffinic functionality in the oils of this invention. Note that if the aromatics content was not measured, it was assumed to be less than 0.1 wt % and not included in the calculation for total weight percent of molecules with cycloparaffinic functionality.

In one embodiment, the oil fractions derived from highly paraffinic wax have a weight percent of molecules with monocycloparaffinic functionality of greater than or equal to 10, preferably greater than 15, and a weight percent of molecules with monocycloparaffinic functionality of less than or equal to 3, preferably less than or equal to 2.5 and more preferably less than or equal to 1.5. Preferably, the oil fractions derived from highly paraffinic wax also have a ratio of weight percent of molecules with monocycloparaffinic functionality to weight percent of molecules with multicycloparaffinic functionality greater than 5, preferably greater than 15, more preferably greater than 50.

The modified ASTM D 5292-99 and HPLC-UV test methods used to measure low level aromatics, and the FIMS test method used to characterize saturates are described in D. C. Kramer, et al., "Influence of Group II & III Base Oil Composition on VI and Oxidation Stability," presented at the 1999 AIChE Spring National Meeting in Houston, Mar. 16, 1999, the contents of which is incorporated herein in its entirety.

Although the highly paraffinic wax feeds are essentially free of olefins, oil processing techniques can introduce olefins, especially at high temperatures, due to 'cracking' reactions. In the presence of heat or UV light, olefins can polymerize to form higher molecular weight products that can color the oil or cause sediment. In general, olefins can be removed during the process of this invention by hydrofinishing or by clay treatment.

The properties of exemplary Fischer-Tropsch oils suitable for use as dielectric fluids are summarized in Table II in the Examples.

The dielectric fluid of the present invention may comprise two or more desired oil fractions having a $T_{90} \geqq 950°$ F. to provide a dielectric fluid having a dielectric breakdown of greater than about 25 kV. Alternatively, the dielectric fluid of the present invention may additionally comprise one or more additional oils. The dielectric fluids comprising two or more desired oil fractions or one or more additional oil will have a Boiling Range Distribution (5-95) greater than about 200° F. The dielectric fluid of the present invention may further comprise one or more additives.

Additives

The dielectric fluids according to the present invention may further comprise one or more additives. As such, the oil fractions derived from highly paraffinic wax, as described herein, are blended with one or more additives to provide a dielectric fluid. When used, the one or more additives are present in an effective amount. The effective amount of additives or additives used in the dielectric fluid is that amount that imparts the desired property or properties. It is undesirable to include an amount of additives in excess of the effective amount. The effective amount of additives is relatively small, generally less than 1.5 weight % of the dielectric fluid, preferably less than 1.0 weight %, as the dielectric fluids of the present invention are very responsive to small amounts of additives.

The additives that may be used with the dielectric fluids of the present invention comprise pour point depressants, antioxidants, and metal deactivators (also known as metal passivators when they deactivate copper). A review of the different classes of lubricant base oil additives may be found in "Lubricants and Lubrication", edited by Theo Mang and Wilfried Dresel, pp. 85-114.

Pour point depressants lower the pour point of oils by reducing the tendency of wax, suspended in the oils, to form crystals or a solid mass in the oils, thus preventing flow. Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. Pour point depressants are disclosed in U.S. Pat. Nos. 4,880,553 and 4,753,745, which are incorporated herein by reference. The amount of pour point depressants added is preferably between about 0.01 to about 1.0 weight percent of the dielectric fluid of the present invention.

Excellent oxidation stability is an important property for dielectric fluids. Dielectric fluids without sufficient oxidation stability are oxidized under the influence of excessive temperature and oxygen, particularly in the presence of small metal particles, which act as catalysts. With time, the oxidation of the oil can result in sludge and deposits. In the worst case scenario, the oil canals in the equipment become blocked and the equipment overheats, which further exacerbates oil oxidation. Oil oxidation may produce charged by-products, such as acids and hydroperoxides, which tend to reduce the insulating properties of the dielectric fluid. Due to the low content of molecules with multicycloparaffinic functionality, the dielectric fluids of the present invention generally have excellent oxidation stability without the addition of antioxidant. However, when additional oxidation stability is desired, antioxidants may be added. Examples of antioxidants useful in the present invention are phenolics, aromatic amines, compounds containing sulfur and phosphorus, organosulfur compounds, organophosphorus compounds, and mixtures thereof. The amount of antioxidants added is preferably between about 0.001 to about 0.3 weight % of the dielectric fluid of the present invention.

Metal deactivators that passivate copper in combination with antioxidants show strong synergistic effects as they prevent the formation of copper ions, suppressing their behavior as pro-oxidants. Metal deactivators useful in the present invention comprise triazoles, benzotriazoles, tolyltriazoles, and tolyltriazole derivatives. The amount of metal deactivators added is preferably between about 0.005 to about 0.8 weight % of the dielectric fluid of the present invention.

An example of an additive system that may be useful in the dielectric fluid of the present invention is disclosed in U.S. Pat. No. 6,083,889, incorporated herein by reference.

The dielectric fluid comprising one or more oil fractions derived from highly paraffinic wax and one or more additives may be made by blending the oil fraction derived from highly paraffinic wax and the one or more additives by techniques known to those of skill in the art. The dielectric fluid components may be blended in a single step going from the individual components (i.e., a Fischer-Tropsch derived oil fraction, a pour point depressant, and an antioxidant) directly to provide the dielectric fluid. In the alternative, the oil fraction derived from highly paraffinic wax and one additive (i.e., the pour point depressant) may be blended initially and then the resulting blend may be mixed with a second additive (i.e., the antioxidant). The blend of the oil fraction derived from highly paraffinic wax and the first additive may be isolated as such or the addition of the second additive may occur immediately.

Additional Oil

The dielectric fluids according to the present invention may further comprise one or more other oils typically used as dielectric fluids. These other oils may be Fischer-Tropsch derived oils, mineral oil, other synthetic oils, and mixtures thereof. The use of more than one oil allows for upgrading of a less desirable property of one oil with the addition of a second oil having a more preferred property. Examples of properties that may be upgraded with blending are viscosity, pour point, flash and fire points, interfacial tension, and dielectric breakdown.

As such, the oil fractions derived from highly paraffinic wax, as described herein, are blended with one or more other oils to provide a dielectric fluid. When a second oil is used, the dielectric fluids according to the present invention can comprise 5 to 99 weight % oil fraction derived from a highly paraffinic wax and 1 to 95 weight % second oil.

When another oil is used, the dielectric fluids according to the present invention may be made by blending the oil fraction derived from highly paraffinic wax with one or more additional oils and optionally one or more additives by techniques known to those of skill in the art. The dielectric fluid components may be blended in a single step going from the individual components directly to provide the dielectric fluid. In the alternative, the oil fraction derived from highly paraffinic wax and one additive may be blended initially and then the resulting blend may be mixed with the second oil. The blend of the oil fraction derived from highly paraffinic wax and the first additive may be isolated as such or the addition of the second oil may occur immediately.

The oil fraction derived from highly paraffinic wax used may be manufactured at a site different from the site at which the components of the dielectric fluid are received and blended. In one embodiment the oil fraction is derived from a Fischer Tropsch process at one site, and the dielectric fluid is blended at a site which is different from the site at which the Fischer-Tropsch derived oil fraction is originally made. Furthermore, the components of the dielectric fluid (i.e., the Fischer-Tropsch derived oil fraction, the additional oils, and the additives) may all be manufactured at different sites. Preferably, the Fischer-Tropsch derived oil fraction is manufactured at a remote site (i.e., a location away from a refinery or market, which location may have a higher cost of construction than the cost of construction at the refinery or market. In quantitative terms, the distance of transportation between the remote site and the refinery or market is at least 100 miles, preferably more than 500 miles, and most preferably more than 1000 miles).

Preferably, the Fischer-Tropsch derived oil is manufactured at a first remote site and shipped to a second site. The additional oils to be included in the dielectric fluid may be manufactured at a site that is the same as the first remote site or at a third remote site. The second site receives the Fischer-Tropsch derived oil fraction, the additional oils, and the additives. The dielectric fluid is manufactured at this second site.

EXAMPLES

The invention will be further explained by the following illustrative examples that are intended to be non-limiting.

Samples of hydrotreated Fischer-Tropsch product made using a Fe-based Fischer-Tropsch synthesis catalyst and a Co-based Fischer-Tropsch catalyst were analyzed and found to have the properties shown in Table I.

TABLE I

| | Fischer-Tropsch Waxes | |
|---|---|---|
| | Fe-Based | Co-Based |
| N-Paraffin Analysis by GC, Wt % | 92.15 | Not tested |
| Nitrogen, Wt % | <8 | <2 |
| Sulfur, Wt % | <2 | <2 |
| Oxygen, Wt % (Neutron Activation) | 0.15 | 0.08 |
| Oil Content, D 721, Wt % | <0.8 | Not tested |
| Pour Point, ° C. | 82 | Not tested |
| SIMDIST TBP (Weight %), ° F. | | |
| $T_{0.5}$ | 784 | 414 |
| $T_5$ | 853 | 565 |
| $T_{10}$ | 875 | 596 |
| $T_{20}$ | 914 | 667 |
| $T_{30}$ | 941 | 710 |
| $T_{40}$ | 968 | 749 |
| $T_{50}$ | 995 | 787 |
| $T_{60}$ | 1013 | 822 |
| $T_{70}$ | 1031 | 867 |
| $T_{80}$ | 1051 | 910 |
| $T_{90}$ | 1081 | 969 |
| $T_{95}$ | 1107 | 1002 |
| $T_{99.5}$ | 1133 | 1065 |
| Weight % $C_{30+}$ | 96.9 | 45.8 |
| Weight % $C_{60+}$ | 0.55 | 3.12 |
| $C_{60+}/C_{30+}$ | 0.01 | 0.07 |

The Fischer-Tropsch waxes had a weight ratio of compounds having at least 60 carbons atoms to compounds having at least 30 carbon atoms of less than 0.18 and a $T_{90}$ boiling point greater than about 950° F. The Fe-based wax was hydroisomerized over a Pt/SSZ-32 catalyst or Pt/SAPO-11 catalyst which contained between 0.2 and 0.5 wt % Pt on an alumina oxide support. Run conditions were between 670 and 685° F., 1.0 $hr^{-1}$ LHSV, 1000 psig reactor pressure, and a once-through hydrogen rate of between 2 and 7 MSCF/bbl. The reactor effluent passed directly to a second reactor, also at 1000 psig, which contained a Pt/Pd on silica-alumina hydrofinishing catalyst. Conditions in that reactor were a temperature of 450° F. and LHSV of 1.0 $hr^{-1}$.

The products boiling above 650° F. were fractionated by vacuum distillation to produce oil fractions of different viscosity grades. Test data on specific distillation cuts useful as oil fractions in the present invention are shown in Table II.

Four Fischer-Tropsch derived oil fractions were tested: FT-6.3, FT-7.5, FT-10, and FT-14. Test data on the specific fractions useful as the dielectric fluid of the present invention are shown below in Table II.

TABLE II

| | Fischer-Tropsch Derived Oils | | | |
|---|---|---|---|---|
| Properties | FT-6.3 | FT-7.5 | FT-10 | FT-14 |
| Catalyst Type | SAPO-11 | SSZ-32 | SAPO-11 | SAPO-11 |
| Kinematic Viscosity at 40° C., cSt | 30.85 | 37.68 | 55.93 | 95 |

TABLE II-continued

| Properties | FT-6.3 | FT-7.5 | FT-10 | FT-14 |
|---|---|---|---|---|
| | Fischer-Tropsch Derived Oils | | | |
| Kinematic Viscosity at 100° C., cSt | 6.26 | 7.468 | 9.83 | 14.62 |
| Viscosity Index, D2270 | 158 | 170 | 163 | 160 |
| Pour Point, ° C., D5950 | −12 | −9 | −12 | −1 |
| Aromatics, Wt % | Not meas. | Not meas. | 0.0162 | Not meas. |
| Olefins by Proton NMR, Wt % | 1.1 | 2.8 | 0.0 | 0.7 |
| Noack Volatility, Wt % | <3 | <5 | <1 | <0.5 |
| Aniline Point, ° C., D611 | | | 137 | |
| Simulated TBP (Weight %), ° F., D6352 | | | | |
| $T_{0.5}$ (Initial Boiling Point) | 832 | 701 | 887 | 955 |
| $T_5$ | 853 | 754 | 911 | 977 |
| $T_{10}$ | 863 | 796 | 921 | 986 |
| $T_{20}$ | 879 | 847 | 936 | 999 |
| $T_{30}$ | 892 | 881 | 948 | 1009 |
| $T_{40}$ | 904 | 908 | 959 | 1020 |
| $T_{50}$ | 915 | 933 | 971 | 1034 |
| $T_{60}$ | 926 | 958 | 985 | 1047 |
| $T_{70}$ | 938 | 985 | 999 | 1064 |
| $T_{80}$ | 950 | 1012 | 1013 | 1092 |
| $T_{90}$ | 967 | 1045 | 1050 | 1153 |
| $T_{95}$ | 979 | 1074 | 1074 | 1208 |
| $T_{99.5}$ (Final Boiling Point) | 1006 | 1139 | 1137 | 1300 |

TABLE II-continued

| Properties | FT-6.3 | FT-7.5 | FT-10 | FT-14 |
|---|---|---|---|---|
| | Fischer-Tropsch Derived Oils | | | |
| Boiling Range Distribution (5–95) | 126 | 320 | 163 | 231 |
| FIMS Analysis, Weight % | | | | |
| Alkanes | 76.9 | 81.4 | 81.3 | 76.0 |
| 1-Unsaturations | 22.6 | 18.6 | 16.4 | 22.1 |
| 2-Unsaturations | 0.4 | 0.0 | 1.7 | 1.8 |
| 3-Unsaturations | 0.0 | 0.0 | 0.0 | 0.0 |
| 4-Unsaturations | 0.0 | 0.0 | 0.6 | 0.2 |
| 5-Unsaturations | 0.0 | 0.0 | 0.0 | 0.0 |
| 6-Unsaturations | 0.0 | 0.0 | 0.0 | 0.0 |
| Total | 99.9 | 100.0 | 100.0 | 100.1 |
| Molecules with Cycloparaffinic Functionality, Weight % by FIMS | 21.9 | 15.8 | 18.7 | 23.4 |
| Molecules with Multicycloparaffinic Functionality, Weight % by FIMS | 0.4 | 0.0 | 2.3 | 2.0 |

Two of the oils, FT-10, and FT-14, were each blended with 0.2 weight % Viscoplex® Series 1 (polymethacrylate) pour point depressant. Additionally, a mixture of 70 weight % FT-14 and 30 weight % FT-10 was blended with 0.2 weight % Viscoplex® Series 1 (polymethacrylate) pour point depressant. The properties of these samples are shown in Table III.

TABLE III

| Performance Tests | ASTM D3487 | ASTM D5222 | IEEE C57.121 | IEC 1099 | FT-10 | FT-14 | 70% FT-14 30% FT-10 |
|---|---|---|---|---|---|---|---|
| | Dielectric Fluids | | | | | | |
| | Specification Standards | | | | GTL Oils | | |
| Weight % Pour Point Depressant | | | | | 0.2 | 0.2 | 0.2 |
| Physical Properties | | | | | | | |
| Kinematic Viscosity at 40° C., cSt | ≦12.0 | ≦130 | 100–130 | ≦35 | | | |
| Kinematic Viscosity at 100° C., cSt | ≦3.0 | ≦14.0 | 10–14 | * | | | |
| Pour Point, ° C., D5950 | ≦−40 | ≦−21 | ≦−21 | ≦−45 | −24 | −18 | −21 |
| Appearance @ 25° C., Visual | Bright & Clear | Bright & Clear | * | * | Bright & Clear | Cloudy | Cloudy |
| Flash Point, ° C., D92 | >145 | ≧275 | ≧275 | ≧250 | | | 294 |
| Fire Point, ° C., D92 | * | ≧300 | ≧300 | ≧300 | | | 328 |
| Chemical Properties | | | | | | | |
| Interfacial Tension, dyne/cm | ≧40 | ≧40 | ≧38–40 | * | 47.0 | 35.8 | 41.1 |
| Neutralization Number, mg KOH/g | ≦0.03 | ≦0.03 | ≦0.03 | ≦0.03 | 0.010 | 0.030 | 0.024 |
| Water Content, ppm, D1533 | ≦35 | ≦35 | ≦25 | ≦200 | 23 | 30 | 25 |
| Dielectric Properties | | | | | | | |
| Dielectric Breakdown, kV, D877 | ≧30 | ≧30 | ≧25–30 | * | 27 | 46 | 29 |

TABLE III-continued

| Performance Tests | Dielectric Fluids: Specification Standards: ASTM D3487 | ASTM D5222 | IEEE C57.121 | IEC 1099 | GTL Oils: FT-10 | FT-14 | 70% FT-14 30% FT-10 |
|---|---|---|---|---|---|---|---|
| Dissipation Factor, %, D924 | | | | | | | |
| @25° C. | ≦0.05 | ≦0.05 | ≦0.05–0.1 | * | 0.011 | 0.003 | 0.023 |
| @100° C. | ≦0.30 | ≦0.30 | ≦0.30–1.0 | ≦2.5 | 0.25 | 0.26 | 0.18 |

* No Specification Available

The three samples in Table III exhibit properties making them good non-limiting examples of the dielectric fluids of the present invention. In addition, the blend prepared with FT-10 and FT-14 also has very high flash and fire points, making it a good example of a high fire point dielectric fluid of the present invention. These examples also demonstrate the effectiveness of relatively small amounts of polymethacrylate pour point depressant at reducing pour point.

While the present invention has been described with reference to specific embodiments, this application is intended to cover those various changes and substitutions that may be made by those of ordinary skill in the art without departing from the spirit and scope of the appended claim.

What is claimed is:

1. A process for producing a dielectric fluid comprising:

a) providing a highly paraffinic wax;

b) hydroisomerizing the highly paraffinic wax using a shape selective intermediate pore size molecular sieve comprising a noble metal hydrogenation component under conditions of about 600° F. to about 750° F. to provide an isomerized oil; and c) fractionating the isomerized oil to provide at least one oil fraction having a $T_{90}$ boiling point ≧950° F., a kinematic viscosity between about 6 cSt and about 20 cSt at 100° C., and a pour point of ≧−14° C., wherein the oil comprises ≧10 weight % molecules with monocycloparaffinic functionality, ≦3 weight % molecules with multicycloparaffinic functionality, and less than 0.30 weight % aromatics d) optionally blending the oil fraction with an effective amount of one or more additives; and e) isolating a dielectric fluid having a dielectric breakdown of ≧25 kV as measured by ASTM D877.

2. The process of claim 1, wherein the highly paraffinic wax is derived from a Fischer-Tropsch process.

3. The process of claim 1, wherein the noble metal hydrogenation component is platinum, palladium, or combinations thereof.

4. The process of claim 1, wherein the shape selective intermediate pore size molecular sieve is selected from the group consisting of SAPO-11, SAPO-31, SAPO-41, SM-3, ZSM-22, ZSM-23, ZSM-35, ZSM-48, ZSM-57, SSZ-32, offretite, ferrierite, and combinations thereof.

5. The process of claim 1, wherein the oil fraction comprises ≦2.5 weight % molecules with multicycloparaffinic functionality.

6. The process of claim 1, wherein the oil fraction comprises ≦1.5 weight % molecules with multicycloparaffinic functionality.

7. The process of claim 1, wherein the oil fraction comprises a ratio of weight % of molecules with monocycloparaffinic functionality to weight % of molecules with multicycloparaffinic functionality of greater than 5.

8. The process of claim 1, wherein the oil fraction comprises a ratio of weight % of molecules with monocycloparaffinic functionality to weight % of molecules with multicycloparaffinic functionality of greater than 15.

9. The process of claim 1, wherein the oil fraction comprises a ratio of weight % of molecules with monocycloparaffinic functionality to weight % of molecules with multicycloparaffinic functionality of greater than 50.

10. The process of claim 1, wherein the oil fraction has a $T_{90}$ of greater than about 1000° F.

11. The process of claim 1, wherein the oil fraction has a pour point of ≧−12° C.

12. The process of claim 1, wherein the dielectric fluid has a dielectric breakdown of ≧30 kV as measured by ASTM D877.

13. The process of claim 1, wherein the dielectric fluid has a dielectric breakdown of ≧40 kV as measured by ASTM D877.

14. The process of claim 1, wherein the dielectric fluid has a fire point of ≧310° C.

15. The process of claim 1, wherein the dielectric fluid has a fire point of ≧325° C.

16. The process of claim 1, wherein the dielectric fluid has a flash point of ≧280° C.

17. The process of claim 1, wherein the oil fraction has a 5-95 Boiling Range Distribution of ≧150° F.

18. The process of claim 1, further comprising blending the oil fraction with an effective amount of one or more additives selected from the group consisting of pour point depressants, antioxidants, metal deactivators, and mixtures thereof to the one or more lubricant base oil fractions.

19. The process of claim 18, wherein the effective amount of additives is less than 1 weight %.

20. The process of claim 18, wherein the additive is a pour point depressant and the pour point depressant is in an amount between about 0.01 to about 1.0 weight %.

21. The process of claim 20, wherein the pour point depressant is selected from the group consisting of polymethacrylates; polyacrylates; polyacrylamides; condensation products of haloparaffin waxes and aromatic compounds; vinyl carboxylate polymers; terpolymers of dialkylfumarates, vinyl esters of fatty acids, and alkyl vinyl ethers; and mixtures thereof.

22. The process of claim 18, wherein the additive is an antioxidant and the antioxidant is in an amount between about 0.001 to about 0.3 wt %.

23. The process of claim 21, wherein the antioxidant is selected from the group consisting of phenolics, aromatic amines, compounds containing sulfur and phosphorus, organosulfur compounds, organophosphorus compounds, and mixtures thereof.

24. The process of claim 18, wherein the additive is a metal deactivator and the metal deactivator is in an amount between about 0.005 to about 0.8 wt %.

25. The process of claim 24, wherein the metal deactivator is selected from the group consisting of triazoles, benzotriazoles, tolyltriazoles, tolyltriazole derivatives, and mixtures thereof.

26. The process of claim 1, further comprising blending the oil fraction with a second oil.

27. The process of claim 26, wherein the second oil is selected from the group consisting of Fischer-Tropsch derived oils, mineral oil, other synthetic oils, and mixtures thereof.

28. A process for producing a dielectric fluid comprising:

a) performing a Fischer-Tropsch synthesis to provide a product stream;

b) isolating from the product stream a substantially paraffinic wax feed;

c) hydroisomerizing the substantially paraffinic waxy feed using a shape selective intermediate pore size molecular sieve comprising a noble metal hydrogenation component under conditions of about 600° F. to about 750° F.;

d) isolating an isomerized oil;

e) fractionating the isomerized oil to provide one or more oil fractions having a $T_{90}$ boiling point ≧950° F., a kinematic viscosity between about 6 cSt and about 16 cSt at 100° C., and a pour point of ≧−14° C.; wherein the lubricant base oil comprises ≧10 weight % molecules with monocycloparaffinic functionality, ≦3 weight % molecules with multicycloparaffinic functionality, and less than 0.30 weight % aromatics;

f) optionally blending the one or more oil fractions with an effective amount of one or more additives; and g) isolating a dielectric fluid having a dielectric breakdown of ≧25 kV as measured by ASTM D877.

29. The process of claim 28, wherein the noble metal hydrogenation component is platinum, palladium, or combinations thereof.

30. The process of claim 28, wherein the shape selective intermediate pore size molecular sieve is selected from the group consisting of SAPO-11, SAPO-31, SAPO-41, SM-3, ZSM-22, ZSM-23, ZSM-35, ZSM-48, ZSM-57, SSZ-32, offretite, ferrierite, and combinations thereof.

31. The process of claim 28, wherein the isomerized oil is fractionated by vacuum distillation.

32. The process of claim 28, further comprising blending the one or more oil fractions with an effective amount of one or more additives selected from the group consisting of pour point depressants, antioxidants, metal deactivators, and mixtures thereof to the one or more lubricant base oil fractions.

33. The process of claim 32, wherein the effective amount of additives is less than 1 weight %.

34. The process of claim 28, further comprising blending the one or more oil fractions with a second oil.

35. The process of claim 34, wherein the dielectric fluid has a 5-95 Boiling Range Distribution of ≧200° F.

* * * * *